US012747281B2

(12) United States Patent
Grossman et al.

(10) Patent No.: US 12,747,281 B2
(45) Date of Patent: Sep. 29, 2026

(54) **EXPRESSION OF THE HUMAN LEKTI GENE FROM THE CHROMOSOME OF *STAPHYLOCOCCUS ePIDERMIDIS***

(71) Applicant: Azitra Inc, Branford, CT (US)

(72) Inventors: Trudy H. Grossman, Branford, CT (US); Alexander Tikhonov, Branford, CT (US)

(73) Assignee: Azitra Inc, Branford, CT (US)

( * ) Notice: Subject to any disclaimer, the term of this patent is extended or adjusted under 35 U.S.C. 154(b) by 712 days.

(21) Appl. No.: 18/163,084

(22) Filed: Feb. 1, 2023

(65) Prior Publication Data

US 2024/0092869 A1 Mar. 21, 2024

Related U.S. Application Data

(60) Provisional application No. 63/305,458, filed on Feb. 1, 2022.

(51) Int. Cl.

| | |
|---|---|
| ***C07K 14/81*** | (2006.01) |
| ***A61K 38/57*** | (2006.01) |
| ***A61K 48/00*** | (2006.01) |
| ***C07K 14/32*** | (2006.01) |

(52) U.S. Cl.
CPC .......... *C07K 14/8135* (2013.01); *A61K 38/57* (2013.01); *A61K 48/0075* (2013.01); *C07K 14/32* (2013.01); *C07K 2319/036* (2013.01)

(58) Field of Classification Search
CPC .................................................. C07K 14/8135
See application file for complete search history.

(56) References Cited

U.S. PATENT DOCUMENTS

| | | | | |
|---|---|---|---|---|
| 2017/0073620 | A1 | 3/2017 | Ayangbile et al. | |
| 2017/0275596 | A1 | 9/2017 | Amit et al. | |
| 2019/0040116 | A1* | 2/2019 | Whitfill | A61K 35/745 |
| 2019/0256935 | A1 | 8/2019 | Whitfill et al. | |
| 2021/0070823 | A1 | 3/2021 | Whitfill | |
| 2021/0162029 | A1 | 6/2021 | Sampson | |

FOREIGN PATENT DOCUMENTS

| | | | | |
|---|---|---|---|---|
| CN | 102329766 | A | 1/2012 | |
| WO | 1996/040979 | A1 | 12/1996 | |
| WO | WO-2020206221 | A1 * | 10/2020 | A61K 9/0014 |
| WO | 2021/092043 | A1 | 5/2021 | |
| WO | 2022/165420 | A1 | 8/2022 | |
| WO | 2022/272132 | A2 | 12/2022 | |

OTHER PUBLICATIONS

Le Loir, Yves, et al. "A nine-residue synthetic propeptide enhances secretion efficiency of heterologous proteins in Lactococcus lactis." Journal of Bacteriology 180.7 (1998): 1895-1903. (Year: 1998).*

Janzon et al., The role of the delta-lysin gene (hld) in the regulation of virulence genes by the accessory gene regulator (agr) in *Staphylococcus aureus*. EMBO J. May 1990;9(5):1391-9.

International Search Report and Written Opinion for Application No. PCT/US2023/012133, dated May 23, 2023, 15 pages.

* cited by examiner

*Primary Examiner* — Robert J Yamasaki
(74) *Attorney, Agent, or Firm* — McCarter & English, LLP; Jonathan M. Sparks

(57) ABSTRACT

The present disclosure provides, inter alia, engineered microbes expressing one or more therapeutic proteins from a nucleotide sequence chromosomally integrated, which is effective to treat or ameliorate a disease or disorder, e.g., a skin disease. In certain embodiments, composition, methods, and kits are provided comprising microbes expressing one or more therapeutic proteins from a chromosomally integrated nucleotide sequence.

15 Claims, 6 Drawing Sheets

Specification includes a Sequence Listing.

SE352

27a

SEQUENCE LISTING

```
Sequence total quantity: 135
SEQ ID NO: 1            moltype =   length =
SEQUENCE: 1
000

SEQ ID NO: 2            moltype =   length =
SEQUENCE: 2
000

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype =   length =
SEQUENCE: 6
000

SEQ ID NO: 7            moltype =   length =
SEQUENCE: 7
000

SEQ ID NO: 8            moltype =   length =
SEQUENCE: 8
000

SEQ ID NO: 9            moltype = AA  length = 25
FEATURE                 Location/Qualifiers
REGION                  1..25
                        note = Synthetic: secretion peptide signal
source                  1..25
                        mol_type = protein
                        organism = synthetic construct
SEQUENCE: 9
MKKLAFAITA ASGAAAVLSH HDAEA                                         25

SEQ ID NO: 10           moltype = AA  length = 30
FEATURE                 Location/Qualifiers
REGION                  1..30
                        note = Synthetic: secretion peptide signal
source                  1..30
                        mol_type = protein
                        organism = synthetic construct
SEQUENCE: 10
WLDNRAFSKK FVPVVMATSV ALFFLNLAFA                                    30

SEQ ID NO: 11           moltype = AA  length = 29
FEATURE                 Location/Qualifiers
REGION                  1..29
                        note = Synthetic: secretion peptide signal
source                  1..29
                        mol_type = protein
                        organism = synthetic construct
SEQUENCE: 11
MAKKFNYKLP SMVALTLFGT AFTAHQANA                                     29

SEQ ID NO: 12           moltype = AA  length = 27
FEATURE                 Location/Qualifiers
```

```
REGION                  1..27
                        note = Synthetic: secretion peptide signal
source                  1..27
                        mol_type = protein
                        organism = synthetic construct
SEQUENCE: 12
MKKRFLSICT MTIAALATTT MVNTSYA                                          27

SEQ ID NO: 13           moltype = AA  length = 30
FEATURE                 Location/Qualifiers
REGION                  1..30
                        note = Synthetic: secretion peptide signal
source                  1..30
                        mol_type = protein
                        organism = synthetic construct
SEQUENCE: 13
NLKKQSKLIL IFICIFTFFI MIIQSQFLMG                                       30

SEQ ID NO: 14           moltype = AA  length = 26
FEATURE                 Location/Qualifiers
REGION                  1..26
                        note = Synthetic: secretion peptide signal
source                  1..26
                        mol_type = protein
                        organism = synthetic construct
SEQUENCE: 14
MKIFKLTSLT LAALTLAFPF SHVAQA                                           26

SEQ ID NO: 15           moltype = AA  length = 27
FEATURE                 Location/Qualifiers
REGION                  1..27
                        note = Synthetic: secretion peptide signal
source                  1..27
                        mol_type = protein
                        organism = synthetic construct
SEQUENCE: 15
MKKTVIASTL AVSLGIAGYG LSGHEAH                                          27

SEQ ID NO: 16           moltype = AA  length = 27
FEATURE                 Location/Qualifiers
REGION                  1..27
                        note = Synthetic: secretion peptide signal
source                  1..27
                        mol_type = protein
                        organism = synthetic construct
SEQUENCE: 16
MKKNKFLVYL LSTALITPTF ATQTAFA                                          27

SEQ ID NO: 17           moltype = AA  length = 35
FEATURE                 Location/Qualifiers
REGION                  1..35
                        note = Synthetic: secretion peptide signal
source                  1..35
                        mol_type = protein
                        organism = synthetic construct
SEQUENCE: 17
MKTRQNKYSI RKFSVGASSI LIAALLFMGG GSAQA                                 35

SEQ ID NO: 18           moltype = AA  length = 37
FEATURE                 Location/Qualifiers
REGION                  1..37
                        note = Synthetic: secretion peptide signal
source                  1..37
                        mol_type = protein
                        organism = synthetic construct
SEQUENCE: 18
MKNNNETRRF SIRKYTVGVV SIITGITIFV SGQHAQA                               37

SEQ ID NO: 19           moltype = AA  length = 30
FEATURE                 Location/Qualifiers
REGION                  1..30
                        note = Synthetic: secretion peptide signal
source                  1..30
                        mol_type = protein
                        organism = synthetic construct
SEQUENCE: 19
MKKKLSYMIT IMLAFTLSLA LGLFFNSAHA                                       30

SEQ ID NO: 20           moltype = AA  length = 45
```

```
FEATURE                 Location/Qualifiers
REGION                  1..45
                        note = misc_feature - Serine-aspartate repeat-containing
                         protein F
source                  1..45
                        mol_type = protein
                        organism = Staphylococcus epidermidis
SEQUENCE: 20
MKKRRQGPIN KRVDFLSNKV NKYSIRKFTV GTASILVGAT LMFGA                  45

SEQ ID NO: 21           moltype = AA  length = 27
FEATURE                 Location/Qualifiers
REGION                  1..27
                        note = misc_feature - Glutamyl endopeptidase
source                  1..27
                        mol_type = protein
                        organism = Staphylococcus epidermidis
SEQUENCE: 21
MKKRFLSICT MTIAALATTT MVNTSYA                                      27

SEQ ID NO: 22           moltype = AA  length = 29
FEATURE                 Location/Qualifiers
REGION                  1..29
                        note = misc_feature - Bifunctional autolysin
source                  1..29
                        mol_type = protein
                        organism = Staphylococcus epidermidis
SEQUENCE: 22
MAKKFNYKLP SMVALTLFGT AFTAHQANA                                    29

SEQ ID NO: 23           moltype = AA  length = 50
FEATURE                 Location/Qualifiers
REGION                  1..50
                        note = misc_feature - Serine-aspartate repeat-containing
                         protein G
source                  1..50
                        mol_type = protein
                        organism = Staphylococcus epidermidis
SEQUENCE: 23
MIKKNNLLTK KKPIANKSNK YAIRKFTVGT ASIVIGAALL FGLGHNEAKA             50

SEQ ID NO: 24           moltype = AA  length = 30
FEATURE                 Location/Qualifiers
REGION                  1..30
                        note = misc_feature - Biofilm PIA synthesis deacetylase icaB
source                  1..30
                        mol_type = protein
                        organism = Staphylococcus epidermidis
SEQUENCE: 24
MKPFKLIFIS ALMILIMTNA TPISHLNAQA                                   30

SEQ ID NO: 25           moltype = AA  length = 35
FEATURE                 Location/Qualifiers
REGION                  1..35
                        note = misc_feature - Lipase
source                  1..35
                        mol_type = protein
                        organism = Staphylococcus epidermidis
SEQUENCE: 25
MKTRQNKYSI RKFSVGASSI LIAALLFMGG GSAQA                             35

SEQ ID NO: 26           moltype = AA  length = 23
FEATURE                 Location/Qualifiers
REGION                  1..23
                        note = misc_feature - Epidermin leader peptide-processing
                         serine protease epiP
source                  1..23
                        mol_type = protein
                        organism = Staphylococcus epidermidis
SEQUENCE: 26
MNKFKFFIVF LILSLVFLQN EYA                                          23

SEQ ID NO: 27           moltype = AA  length = 50
FEATURE                 Location/Qualifiers
REGION                  1..50
                        note = misc_feature - Fibrinogen-binding protein
source                  1..50
                        mol_type = protein
                        organism = Staphylococcus epidermidis
```

```
SEQUENCE: 27
MINKKNNLLT KKKPIANKSN KYAIRKFTVG TASIVIGATL LFGLGHNEAK            50

SEQ ID NO: 28          moltype = AA  length = 26
FEATURE                Location/Qualifiers
REGION                 1..26
                       note = misc_feature - Staphylococcal secretory antigen ssaA
source                 1..26
                       mol_type = protein
                       organism = Staphylococcus epidermidis
SEQUENCE: 28
MKKIATATIA TAGIATFAFA HHDAQA                                      26

SEQ ID NO: 29          moltype = AA  length = 28
FEATURE                Location/Qualifiers
REGION                 1..28
                       note = misc_feature - Extracellular elastase
source                 1..28
                       mol_type = protein
                       organism = Staphylococcus epidermidis
SEQUENCE: 29
MKNFSKFALT SIAALTVASP LVNTEVDA                                    28

SEQ ID NO: 30          moltype = AA  length = 37
FEATURE                Location/Qualifiers
source                 1..37
                       mol_type = protein
                       organism = Staphylococcus epidermidis
SEQUENCE: 30
MKNNNETRRF SIRKYTVGVV SIITGITIFV SGQHAQA                          37

SEQ ID NO: 31          moltype = AA  length = 19
FEATURE                Location/Qualifiers
REGION                 1..19
                       note = misc_feature - Uncharacterized lipoprotein SE_0145
source                 1..19
                       mol_type = protein
                       organism = Staphylococcus epidermidis
SEQUENCE: 31
MRYLKRITIY ISLLILVSG                                              19

SEQ ID NO: 32          moltype = AA  length = 20
FEATURE                Location/Qualifiers
REGION                 1..20
                       note = misc_feature - Foldase protein prsA
source                 1..20
                       mol_type = protein
                       organism = Staphylococcus epidermidis
SEQUENCE: 32
MKLMNKIIVP VTASALLLGA                                             20

SEQ ID NO: 33          moltype = AA  length = 40
FEATURE                Location/Qualifiers
REGION                 1..40
                       note = misc_feature - Probable cell wall amidase lytH
source                 1..40
                       mol_type = protein
                       organism = Staphylococcus epidermidis
SEQUENCE: 33
MKKIDSWLTK HGLKNRLTLV VIVIFIIFLI LLFMFVNLSD                       40

SEQ ID NO: 34          moltype = AA  length = 19
FEATURE                Location/Qualifiers
REGION                 1..19
                       note = misc_feature - Membrane protein oxaA 2
source                 1..19
                       mol_type = protein
                       organism = Staphylococcus epidermidis
SEQUENCE: 34
MKKKALLPLF LGIMIFLAG                                              19

SEQ ID NO: 35          moltype = AA  length = 28
FEATURE                Location/Qualifiers
REGION                 1..28
                       note = misc_feature - Probable transglycosylase isaA
source                 1..28
                       mol_type = protein
                       organism = Staphylococcus epidermidis
SEQUENCE: 35
```

```
MKKTVIASTL AVSLGIAGYG LSGHEAHA                                  28

SEQ ID NO: 36          moltype = AA  length = 19
FEATURE                Location/Qualifiers
REGION                 1..19
                       note = misc_feature - Probable quinol oxidase subunit 2
source                 1..19
                       mol_type = protein
                       organism = Staphylococcus epidermidis
SEQUENCE: 36
MSKFKSLLLL FGTLILLSG                                            19

SEQ ID NO: 37          moltype = AA  length = 27
FEATURE                Location/Qualifiers
REGION                 1..27
                       note = misc_feature - Probable transglycosylase sceD
source                 1..27
                       mol_type = protein
                       organism = Staphylococcus epidermidis
SEQUENCE: 37
MKKTLVASSL AIGLGVVAGN AGHDAHA                                   27

SEQ ID NO: 38          moltype = AA  length = 29
FEATURE                Location/Qualifiers
REGION                 1..29
                       note = misc_feature - Bifunctional autolysin
source                 1..29
                       mol_type = protein
                       organism = Staphylococcus epidermidis
SEQUENCE: 38
MAKKFNYKLP SMVALTLFGT AFTAHQANA                                 29

SEQ ID NO: 39          moltype = AA  length = 30
FEATURE                Location/Qualifiers
REGION                 1..30
                       note = misc_feature - Extracellular cysteine protease
source                 1..30
                       mol_type = protein
                       organism = Staphylococcus epidermidis
SEQUENCE: 39
MKKKLSYMIT IMLAFTLSLA LGLFFNSAHA                                30

SEQ ID NO: 40          moltype = AA  length = 18
FEATURE                Location/Qualifiers
REGION                 1..18
                       note = misc_feature - Membrane protein oxaA 1
source                 1..18
                       mol_type = protein
                       organism = Staphylococcus epidermidis
SEQUENCE: 40
MHKRLFITLL GFIILLAG                                             18

SEQ ID NO: 41          moltype = AA  length = 19
FEATURE                Location/Qualifiers
REGION                 1..19
                       note = misc_feature - Uncharacterized lipoprotein SE_0144
source                 1..19
                       mol_type = protein
                       organism = Staphylococcus epidermidis
SEQUENCE: 41
MRYLKRITIY ISLLILVSG                                            19

SEQ ID NO: 42          moltype = AA  length = 25
FEATURE                Location/Qualifiers
REGION                 1..25
                       note = misc_feature - N-acetylmuramoyl-L-alanine amidase
                        sle1
source                 1..25
                       mol_type = protein
                       organism = Staphylococcus epidermidis
SEQUENCE: 42
MQKKYITAII GTTALSALAS THAQA                                     25

SEQ ID NO: 43          moltype = AA  length = 22
FEATURE                Location/Qualifiers
REGION                 1..22
                       note = misc_feature - Uncharacterized lipoprotein SE_0142
source                 1..22
                       mol_type = protein
```

```
                         organism = Staphylococcus epidermidis
SEQUENCE: 43
MKHSSKIIVF VSFLILTIFI GG                                           22

SEQ ID NO: 44            moltype = AA  length = 20
FEATURE                  Location/Qualifiers
REGION                   1..20
                         note = misc_feature - Phosphate-binding protein pstS
source                   1..20
                         mol_type = protein
                         organism = Staphylococcus epidermidis
SEQUENCE: 44
MKKWQLVGTT VLGASVLLGA                                              20

SEQ ID NO: 45            moltype = AA  length = 52
FEATURE                  Location/Qualifiers
REGION                   1..52
                         note = misc_feature - Accumulation-associated protein
source                   1..52
                         mol_type = protein
                         organism = Staphylococcus epidermidis
SEQUENCE: 45
MGKRRQGPIN KKVDFLPNKL NKYSIRKFTV GTASILLGST LIFGSSSHEA KA          52

SEQ ID NO: 46            moltype = AA  length = 26
FEATURE                  Location/Qualifiers
REGION                   1..26
                         note = misc_feature - Staphylococcal secretory antigen ssaA
source                   1..26
                         mol_type = protein
                         organism = Staphylococcus epidermidis
SEQUENCE: 46
MKKIATATIA TAGIATFAFA HHDAQA                                       26

SEQ ID NO: 47            moltype = AA  length = 45
FEATURE                  Location/Qualifiers
REGION                   1..45
                         note = misc_feature - Serine-aspartate repeat-containing
                          protein F
source                   1..45
                         mol_type = protein
                         organism = Staphylococcus epidermidis
SEQUENCE: 47
MKKRRQGPIN KRVDFLSNKV NKYSIRKFTV GTASILVGAT LMFGA                  45

SEQ ID NO: 48            moltype = AA  length = 27
FEATURE                  Location/Qualifiers
REGION                   1..27
                         note = misc_feature - Glutamyl endopeptidase
source                   1..27
                         mol_type = protein
                         organism = Staphylococcus epidermidis
SEQUENCE: 48
MKKRFLSICT MTIAALATTT MVNTSYA                                      27

SEQ ID NO: 49            moltype = AA  length = 35
FEATURE                  Location/Qualifiers
REGION                   1..35
                         note = misc_feature - Lipase
source                   1..35
                         mol_type = protein
                         organism = Staphylococcus epidermidis
SEQUENCE: 49
MKTRQNKYSI RKFSVGASSI LIAALLFMGG GSAQA                             35

SEQ ID NO: 50            moltype = AA  length = 28
FEATURE                  Location/Qualifiers
REGION                   1..28
                         note = misc_feature - Extracellular elastase
source                   1..28
                         mol_type = protein
                         organism = Staphylococcus epidermidis
SEQUENCE: 50
MKNFSKFALT SIAALTVASP LVNTEVDA                                     28

SEQ ID NO: 51            moltype = AA  length = 17
FEATURE                  Location/Qualifiers
REGION                   1..17
                         note = misc_feature - Uncharacterized lipoprotein SE_1947
```

```
source                  1..17
                        mol_type = protein
                        organism = Staphylococcus epidermidis
SEQUENCE: 51
MKKVLASATI LSLMLVG                                             17

SEQ ID NO: 52           moltype = AA  length = 22
FEATURE                 Location/Qualifiers
REGION                  1..22
                        note = misc_feature - Uncharacterized lipoprotein
                         SE_0186/SE_0187
source                  1..22
                        mol_type = protein
                        organism = Staphylococcus epidermidis
SEQUENCE: 52
MKYYGKCISY ISILILTFFI GG                                       22

SEQ ID NO: 53           moltype = AA  length = 22
FEATURE                 Location/Qualifiers
REGION                  1..22
                        note = misc_feature - Uncharacterized lipoprotein SERP2423
source                  1..22
                        mol_type = protein
                        organism = Staphylococcus epidermidis
SEQUENCE: 53
MKHSSKIIVF VSFLILTIFI GG                                       22

SEQ ID NO: 54           moltype = AA  length = 30
FEATURE                 Location/Qualifiers
REGION                  1..30
                        note = misc_feature - Biofilm PIA synthesis deacetylase icaB
source                  1..30
                        mol_type = protein
                        organism = Staphylococcus epidermidis
SEQUENCE: 54
MKPFKLIFIS ALMILIMTNA TPISHLNAQA                               30

SEQ ID NO: 55           moltype = AA  length = 19
FEATURE                 Location/Qualifiers
REGION                  1..19
                        note = misc_feature - Probable quinol oxidase subunit 2
source                  1..19
                        mol_type = protein
                        organism = Staphylococcus epidermidis
SEQUENCE: 55
MSKFKSLLLL FGTLILLSG                                           19

SEQ ID NO: 56           moltype = AA  length = 27
FEATURE                 Location/Qualifiers
REGION                  1..27
                        note = misc_feature - Probable transglycosylase sceD
source                  1..27
                        mol_type = protein
                        organism = Staphylococcus epidermidis
SEQUENCE: 56
MKKTLVASSL AIGLGVVAGN AGHDAHA                                  27

SEQ ID NO: 57           moltype = AA  length = 19
FEATURE                 Location/Qualifiers
REGION                  1..19
                        note = misc_feature - Uncharacterized lipoprotein SERP2447
source                  1..19
                        mol_type = protein
                        organism = Staphylococcus epidermidis
SEQUENCE: 57
MHYLKKVTIY ISLLILVSG                                           19

SEQ ID NO: 58           moltype = AA  length = 25
FEATURE                 Location/Qualifiers
REGION                  1..25
                        note = misc_feature - N-acetylmuramoyl-L-alanine amidase
                         sle1
source                  1..25
                        mol_type = protein
                        organism = Staphylococcus epidermidis
SEQUENCE: 58
MQKKYITAII GTTALSALAS THAQA                                    25

SEQ ID NO: 59           moltype = AA  length = 22
```

```
FEATURE               Location/Qualifiers
REGION                1..22
                      note = misc_feature - Uncharacterized lipoprotein SERP2445
source                1..22
                      mol_type = protein
                      organism = Staphylococcus epidermidis
SEQUENCE: 59
MKHSKKLLLC ISFLLITFFI GG                                          22

SEQ ID NO: 60         moltype = AA  length = 26
FEATURE               Location/Qualifiers
REGION                1..26
                      note = misc_feature - Staphylococcal secretory antigen ssaA
source                1..26
                      mol_type = protein
                      organism = Staphylococcus epidermidis
SEQUENCE: 60
MKKIATATIA TAGIATFAFA HHDAQA                                      26

SEQ ID NO: 61         moltype = AA  length = 19
FEATURE               Location/Qualifiers
REGION                1..19
                      note = misc_feature - Uncharacterized lipoprotein SERP2443
source                1..19
                      mol_type = protein
                      organism = Staphylococcus epidermidis
SEQUENCE: 61
MRYLKKVTIY ISLLILVSG                                              19

SEQ ID NO: 62         moltype = AA  length = 27
FEATURE               Location/Qualifiers
REGION                1..27
                      note = misc_feature - Glutamyl endopeptidase
source                1..27
                      mol_type = protein
                      organism = Staphylococcus epidermidis
SEQUENCE: 62
MKKRFLSICT MTIAALATTT MVNTSYA                                     27

SEQ ID NO: 63         moltype = AA  length = 20
FEATURE               Location/Qualifiers
REGION                1..20
                      note = misc_feature - Phosphate-binding protein pstS
source                1..20
                      mol_type = protein
                      organism = Staphylococcus epidermidis
SEQUENCE: 63
MKKWQLVGTT VLGASVLLGA                                             20

SEQ ID NO: 64         moltype = AA  length = 29
FEATURE               Location/Qualifiers
REGION                1..29
                      note = misc_feature - Bifunctional autolysin
source                1..29
                      mol_type = protein
                      organism = Staphylococcus epidermidis
SEQUENCE: 64
MAKKFNYKLP SMVALTLFGT AFTAHQANA                                   29

SEQ ID NO: 65         moltype = AA  length = 30
FEATURE               Location/Qualifiers
REGION                1..30
                      note = misc_feature - Extracellular cysteine protease
source                1..30
                      mol_type = protein
                      organism = Staphylococcus epidermidis
SEQUENCE: 65
MKKKLSYMIT IMLAFTLSLA LGLFFNSAHA                                  30

SEQ ID NO: 66         moltype = AA  length = 18
FEATURE               Location/Qualifiers
REGION                1..18
                      note = misc_feature - Membrane protein oxaA 1
source                1..18
                      mol_type = protein
                      organism = Staphylococcus epidermidis
SEQUENCE: 66
MHKRLFITLL GFIILLAG                                               18
```

```
SEQ ID NO: 67          moltype = AA  length = 22
FEATURE                Location/Qualifiers
REGION                 1..22
                       note = misc_feature - Uncharacterized lipoprotein SERP2422
source                 1..22
                       mol_type = protein
                       organism = Staphylococcus epidermidis
SEQUENCE: 67
MRYLKKVTIY ISLLILTIFI GG                                          22

SEQ ID NO: 68          moltype = AA  length = 17
FEATURE                Location/Qualifiers
REGION                 1..17
                       note = misc_feature - Uncharacterized lipoprotein SERP1959
source                 1..17
                       mol_type = protein
                       organism = Staphylococcus epidermidis
SEQUENCE: 68
MKKVLASATI LSLMLVG                                                17

SEQ ID NO: 69          moltype = AA  length = 22
FEATURE                Location/Qualifiers
REGION                 1..22
                       note = misc_feature - Uncharacterized lipoprotein SERP2453
source                 1..22
                       mol_type = protein
                       organism = Staphylococcus epidermidis
SEQUENCE: 69
MKHSKKLLLC ISFLLITVFI SG                                          22

SEQ ID NO: 70          moltype = AA  length = 22
FEATURE                Location/Qualifiers
REGION                 1..22
                       note = misc_feature - Uncharacterized lipoprotein SERP2465
source                 1..22
                       mol_type = protein
                       organism = Staphylococcus epidermidis
SEQUENCE: 70
MKHSKKLLLC ISFLLITFFI SG                                          22

SEQ ID NO: 71          moltype = AA  length = 28
FEATURE                Location/Qualifiers
REGION                 1..28
                       note = misc_feature - Probable transglycosylase isaA
source                 1..28
                       mol_type = protein
                       organism = Staphylococcus epidermidis
SEQUENCE: 71
MKKTVIASTL AVSLGIAGYG LSGHEAHA                                    28

SEQ ID NO: 72          moltype = AA  length = 22
FEATURE                Location/Qualifiers
REGION                 1..22
                       note = misc_feature - Uncharacterized lipoprotein SERP2451
source                 1..22
                       mol_type = protein
                       organism = Staphylococcus epidermidis
SEQUENCE: 72
MKHSKKLLLC ISFLLITIFI SG                                          22

SEQ ID NO: 73          moltype = AA  length = 40
FEATURE                Location/Qualifiers
REGION                 1..40
                       note = misc_feature - Probable cell wall amidase lytH
source                 1..40
                       mol_type = protein
                       organism = Staphylococcus epidermidis
SEQUENCE: 73
MKKIDSWLTK HGLKNRLTLV VIVIFIIFLI LLFMFVNLSD                       40

SEQ ID NO: 74          moltype = AA  length = 19
FEATURE                Location/Qualifiers
REGION                 1..19
                       note = misc_feature - Membrane protein oxaA 2
source                 1..19
                       mol_type = protein
                       organism = Staphylococcus epidermidis
SEQUENCE: 74
MKKKALLPLF LGIMIFLAG                                              19
```

```
SEQ ID NO: 75           moltype = AA  length = 20
FEATURE                 Location/Qualifiers
REGION                  1..20
                        note = misc_feature - Foldase protein prsA
source                  1..20
                        mol_type = protein
                        organism = Staphylococcus epidermidis
SEQUENCE: 75
MKLMNKIIVP VTASALLLGA                                                20

SEQ ID NO: 76           moltype = AA  length = 35
FEATURE                 Location/Qualifiers
REGION                  1..35
                        note = misc_feature - Lipase
source                  1..35
                        mol_type = protein
                        organism = Staphylococcus epidermidis
SEQUENCE: 76
MKTRQNKYSI RKFSVGASSI LIAALLFMGG GSAQA                               35

SEQ ID NO: 77           moltype = AA  length = 27
FEATURE                 Location/Qualifiers
REGION                  1..27
                        note = Synthetic: secretion peptide signal
source                  1..27
                        mol_type = protein
                        organism = synthetic construct
SEQUENCE: 77
MKKRFLSICT MTIAALATTT MVNTSYA                                        27

SEQ ID NO: 78           moltype = AA  length = 29
FEATURE                 Location/Qualifiers
REGION                  1..29
                        note = Synthetic: secretion peptide signal
source                  1..29
                        mol_type = protein
                        organism = synthetic construct
SEQUENCE: 78
MKKKQVMLAL TAAAGLGLTA LHSAPAAKA                                      29

SEQ ID NO: 79           moltype = AA  length = 18
FEATURE                 Location/Qualifiers
REGION                  1..18
                        note = Synthetic: cell penetrating sequence
source                  1..18
                        mol_type = protein
                        organism = synthetic construct
SEQUENCE: 79
KLALKLALKA LKAALKLA                                                  18

SEQ ID NO: 80           moltype = AA  length = 30
FEATURE                 Location/Qualifiers
REGION                  1..30
                        note = Synthetic: cell penetrating sequence
source                  1..30
                        mol_type = protein
                        organism = synthetic construct
SEQUENCE: 80
WEAKLAKALA KALAKHLAKA LAKALKACEA                                     30

SEQ ID NO: 81           moltype = AA  length = 21
FEATURE                 Location/Qualifiers
REGION                  1..21
                        note = Synthetic: cell penetrating sequence
source                  1..21
                        mol_type = protein
                        organism = synthetic construct
SEQUENCE: 81
KETWWETWWT EWSQPKKKRK V                                              21

SEQ ID NO: 82           moltype = AA  length = 9
FEATURE                 Location/Qualifiers
REGION                  1..9
                        note = Synthetic: cell penetrating sequence
source                  1..9
                        mol_type = protein
                        organism = synthetic construct
SEQUENCE: 82
```

```
RRRRRRRRR                                                         9

SEQ ID NO: 83          moltype = AA  length = 24
FEATURE                Location/Qualifiers
REGION                 1..24
                       note = Synthetic: cell penetrating sequence
source                 1..24
                       mol_type = protein
                       organism = synthetic construct
SEQUENCE: 83
LGTYTQDFNK FHTFPQTAIG VGAP                                        24

SEQ ID NO: 84          moltype = AA  length = 15
FEATURE                Location/Qualifiers
REGION                 1..15
                       note = Synthetic: cell penetrating sequence
source                 1..15
                       mol_type = protein
                       organism = synthetic construct
SEQUENCE: 84
RQIKWFQNRR MKWKK                                                  15

SEQ ID NO: 85          moltype = AA  length = 11
FEATURE                Location/Qualifiers
REGION                 1..11
                       note = Synthetic: cell penetrating sequence
source                 1..11
                       mol_type = protein
                       organism = synthetic construct
SEQUENCE: 85
YGRKKRRQRR R                                                      11

SEQ ID NO: 86          moltype = AA  length = 18
FEATURE                Location/Qualifiers
REGION                 1..18
                       note = Synthetic: cell penetrating sequence
source                 1..18
                       mol_type = protein
                       organism = synthetic construct
SEQUENCE: 86
RGGRLSYSRR RFSTSTGR                                               18

SEQ ID NO: 87          moltype = AA  length = 10
FEATURE                Location/Qualifiers
REGION                 1..10
                       note = Synthetic: cell penetrating sequence
source                 1..10
                       mol_type = protein
                       organism = synthetic construct
SEQUENCE: 87
RRLSYSRRRF                                                        10

SEQ ID NO: 88          moltype = AA  length = 12
FEATURE                Location/Qualifiers
REGION                 1..12
                       note = Synthetic: cell penetrating sequence
source                 1..12
                       mol_type = protein
                       organism = synthetic construct
SEQUENCE: 88
PIRRRKKLRR LK                                                     12

SEQ ID NO: 89          moltype = AA  length = 12
FEATURE                Location/Qualifiers
REGION                 1..12
                       note = Synthetic: cell penetrating sequence
source                 1..12
                       mol_type = protein
                       organism = synthetic construct
SEQUENCE: 89
RRQRRTSKLM KR                                                     12

SEQ ID NO: 90          moltype = AA  length = 15
FEATURE                Location/Qualifiers
REGION                 1..15
                       note = Synthetic: cell penetrating sequence
source                 1..15
                       mol_type = protein
                       organism = synthetic construct
```

```
SEQUENCE: 90
RRRRNRTRRN RRRVR                                                  15

SEQ ID NO: 91           moltype = AA  length = 19
FEATURE                 Location/Qualifiers
REGION                  1..19
                        note = Synthetic: cell penetrating sequence
source                  1..19
                        mol_type = protein
                        organism = synthetic construct
SEQUENCE: 91
KMTRAQRRAA ARRNRWTAR                                              19

SEQ ID NO: 92           moltype = AA  length = 13
FEATURE                 Location/Qualifiers
REGION                  1..13
                        note = Synthetic: cell penetrating sequence
source                  1..13
                        mol_type = protein
                        organism = synthetic construct
SEQUENCE: 92
TRRQRTRRAR RNR                                                    13

SEQ ID NO: 93           moltype = AA  length = 13
FEATURE                 Location/Qualifiers
REGION                  1..13
                        note = Synthetic: cell penetrating sequence
source                  1..13
                        mol_type = protein
                        organism = synthetic construct
SEQUENCE: 93
GRKKRRQRRR PPQ                                                    13

SEQ ID NO: 94           moltype = AA  length = 13
FEATURE                 Location/Qualifiers
REGION                  1..13
                        note = Synthetic: cell penetrating sequence
source                  1..13
                        mol_type = protein
                        organism = synthetic construct
SEQUENCE: 94
GRRRRRRRRR PPQ                                                    13

SEQ ID NO: 95           moltype = AA  length = 27
FEATURE                 Location/Qualifiers
REGION                  1..27
                        note = Synthetic: cell penetrating sequence
source                  1..27
                        mol_type = protein
                        organism = synthetic construct
SEQUENCE: 95
GWTLNSAGYL LGKINLKALA ALAKKIL                                     27

SEQ ID NO: 96           moltype = AA  length = 17
FEATURE                 Location/Qualifiers
REGION                  1..17
                        note = Synthetic: cell penetrating sequence
source                  1..17
                        mol_type = protein
                        organism = synthetic construct
SEQUENCE: 96
KLALKLALKL ALALKLA                                                17

SEQ ID NO: 97           moltype = AA  length = 27
FEATURE                 Location/Qualifiers
REGION                  1..27
                        note = Synthetic: cell penetrating sequence
source                  1..27
                        mol_type = protein
                        organism = synthetic construct
SEQUENCE: 97
MGLGLHLLVL AAALQGAWSQ PKKKRKV                                     27

SEQ ID NO: 98           moltype = AA  length = 27
FEATURE                 Location/Qualifiers
REGION                  1..27
                        note = Synthetic: cell penetrating sequence
source                  1..27
                        mol_type = protein
```

```
                      organism = synthetic construct
SEQUENCE: 98
GALFLGWLGA AGSTMGAWSQ PKKKRKV                                 27

SEQ ID NO: 99         moltype = AA  length = 27
FEATURE               Location/Qualifiers
REGION                1..27
                      note = Synthetic: cell penetrating sequence
source                1..27
                      mol_type = protein
                      organism = synthetic construct
SEQUENCE: 99
GALFLGFLGA AGSTMGAWSQ PKKKRKV                                 27

SEQ ID NO: 100        moltype = AA  length = 27
FEATURE               Location/Qualifiers
REGION                1..27
                      note = Synthetic: cell penetrating sequence
source                1..27
                      mol_type = protein
                      organism = synthetic construct
SEQUENCE: 100
GALFLGFLGA AGSTMGAWSQ PKSKRKV                                 27

SEQ ID NO: 101        moltype = AA  length = 21
FEATURE               Location/Qualifiers
REGION                1..21
                      note = Synthetic: cell penetrating sequence
source                1..21
                      mol_type = protein
                      organism = synthetic construct
SEQUENCE: 101
KETWWETWWT EWSQPKKKRK V                                       21

SEQ ID NO: 102        moltype = AA  length = 21
FEATURE               Location/Qualifiers
REGION                1..21
                      note = Synthetic: cell penetrating sequence
source                1..21
                      mol_type = protein
                      organism = synthetic construct
SEQUENCE: 102
KETWFETWFT EWSQPKKKRK V                                       21

SEQ ID NO: 103        moltype = AA  length = 1064
FEATURE               Location/Qualifiers
REGION                1..1064
                      note = Synthetic: LEKTI amino acid sequence Residues 1-1064
source                1..1064
                      mol_type = protein
                      organism = synthetic construct
SEQUENCE: 103
MKIATVSVLL PLALCLIQDA ASKNEDQEMC HEFQAFMKNG KLFCPQDKKF FQSLDGIMFI  60
NKCATCKMIL EKEAKSQKRA RHLARAPKAT APTELNCDDF KKGERDGDFI CPDYYEAVCG  120
TDGKTYDNRC ALCAENAKTG SQIGVKSEGE CKSSNPEQDV CSAFRPFVRD GRLGCTREND  180
PVLGPDGKTH GNKCAMCAEL FLKEAENAKR EGETRIRRNA EKDFCKEYEK QVRNGRLFCT  240
RESDPVRGPD GRMHGNKCAL CAEIFKQRFS EENSKTDQNL GKAEEKTKVK REIVKLCSQY  300
QNQAKNGILF CTRENDPIRG PDGKMHGNLC SMCQAYFQAE NEEKKKAEAR ARNKRESGKA  360
TSYAELCSEY RKLVRNGKLA CTRENDPIQG PDGKVHGNTC SMCEVFFQAE EEEKKKKEGK  420
SRNKRQSKST ASFEELCSEY RKSRKNGRLF CTRENDPIQG PDGKMHGNTC SMCEAFFQQE  480
ERARAKAKRE AAKEICSEFR DQVRNGTLIC TREHNPVRGP DGKMHGNKCA MCASVFKLEE  540
EEKKNDKEEK GKVEAEKVKR EAVQELCSEY RHYVRNGRLP CTRENDPIEG LDGKIHGNTC  600
SMCEAFFQQE AKEKERAEPR AKVKREAEKE TCDEFRRLLQ NGKLFCTREN DPVRGPDGKT  660
HGNKCAMCKA VFQKENEERK RKEEEDQRNA AGHGSSGGGG GNTQDECAEY REQMKNGRLS  720
CTRESDPVRD ADGKSYNNQC TMCKAKLERE AERKNEYSRS RSNGTGSESG KDTCDEFRSQ  780
MKNGKLICTR ESDPVRGPDG KTHGNKCTMC KEKLEREAAE KKKKEDEDRS NTGERSNTGE  840
RSNDKEDLCR EFRSMQRNGK LICTRENNPV RGPYGKMHIN KCAMCQSIFD REANERKKKD  900
EEKSSSKPSN NAKDECSEFR NYIRNNELIC PRENDPVHGA DGKFYTNKCY MCRAVFLTEA  960
LERAKLQEKP SHVRASQEED SPDSFSSLDS EMCKDYRVLP RIGYLCPKDL KPVCGDDGQT  1020
YNNPCMLCHE NLIRQTNTHI RSTGKCEESS TPGTTAASMP PSDE              1064

SEQ ID NO: 104        moltype = AA  length = 55
FEATURE               Location/Qualifiers
REGION                1..55
                      note = Synthetic: LEKTI Domain 1 (residues 23-77)
source                1..55
                      mol_type = protein
                      organism = synthetic construct
SEQUENCE: 104
```

```
KNEDQEMCHE FQAFMKNGKL FCPQDKKFFQ SLDGIMFINK CATCKMILEK EAKSQ       55

SEQ ID NO: 105         moltype = AA  length = 63
FEATURE                Location/Qualifiers
REGION                 1..63
                       note = Synthetic: LEKTI Domain 2 (residues 91-153)
source                 1..63
                       mol_type = protein
                       organism = synthetic construct
SEQUENCE: 105
APTELNCDDF KKGERDGDFI CPDYYEAVCG TDGKTYDNRC ALCAENAKTG SQIGVKSEGE  60
CKS                                                                63

SEQ ID NO: 106         moltype = AA  length = 62
FEATURE                Location/Qualifiers
REGION                 1..62
                       note = Synthetic: LEKTI Domain 3 (residues 155-216
source                 1..62
                       mol_type = protein
                       organism = synthetic construct
SEQUENCE: 106
NPEQDVCSAF RPFVRDGRLG CTRENDPVLG PDGKTHGNKC AMCAELFLKE AENAKREGET  60
RI                                                                 62

SEQ ID NO: 107         moltype = AA  length = 67
FEATURE                Location/Qualifiers
REGION                 1..67
                       note = Synthetic: LEKTI Domain 4 (residues 219-285)
source                 1..67
                       mol_type = protein
                       organism = synthetic construct
SEQUENCE: 107
NAEKDFCKEY EKQVRNGRLF CTRESDPVRG PDGRMHGNKC ALCAEIFKQR FSEENSKTDQ  60
NLGKAEE                                                            67

SEQ ID NO: 108         moltype = AA  length = 62
FEATURE                Location/Qualifiers
REGION                 1..62
                       note = Synthetic: LEKTI_Domain 5 (residues 291-352)
source                 1..62
                       mol_type = protein
                       organism = synthetic construct
SEQUENCE: 108
REIVKLCSQY QNQAKNGILF CTRENDPIRG PDGKMHGNLC SMCQAYFQAE NEEKKKAEAR  60
AR                                                                 62

SEQ ID NO: 109         moltype = AA  length = 68
FEATURE                Location/Qualifiers
REGION                 1..68
                       note = Synthetic: LEKTI_Domain 6 (residues 356-423)
source                 1..68
                       mol_type = protein
                       organism = synthetic construct
SEQUENCE: 109
ESGKATSYAE LCSEYRKLVR NGKLACTREN DPIQGPDGKV HGNTCSMCEV FFQAEEEEKK  60
KKEGKSRN                                                           68

SEQ ID NO: 110         moltype = AA  length = 59
FEATURE                Location/Qualifiers
REGION                 1..59
                       note = Synthetic: LEKTI Domain 7 (residues 431-489)
source                 1..59
                       mol_type = protein
                       organism = synthetic construct
SEQUENCE: 110
ASFEELCSEY RKSRKNGRLF CTRENDPIQG PDGKMHGNTC SMCEAFFQQE ERARAKAKR   59

SEQ ID NO: 111         moltype = AA  length = 62
FEATURE                Location/Qualifiers
REGION                 1..62
                       note = Synthetic: LEKTI Domain 8 (residues 490-550)
source                 1..62
                       mol_type = protein
                       organism = synthetic construct
SEQUENCE: 111
EAAKEICSEF RDQVRNGTLI CTREHNPVRG PDGKMHGNKC AMCASVFKLE EEEKKNDKEE  60
KG                                                                 62

SEQ ID NO: 112         moltype = AA  length = 62
```

```
FEATURE                Location/Qualifiers
REGION                 1..62
                       note = Synthetic: LEKTI Domain 9 (residues 561-622)
source                 1..62
                       mol_type = protein
                       organism = synthetic construct
SEQUENCE: 112
EAVQELCSEY RHYVRNGRLP CTRENDPIEG LDGKIHGNTC SMCEAFFQQE AKEKERAEPR  60
AK                                                                 62

SEQ ID NO: 113         moltype = AA  length = 63
FEATURE                Location/Qualifiers
REGION                 1..63
                       note = Synthetic: LEKTI Domain 10 (residues 626-688)
source                 1..63
                       mol_type = protein
                       organism = synthetic construct
SEQUENCE: 113
EAEKETCDEF RRLLQNGKLF CTRENDPVRG PDGKTHGNKC AMCKAVFQKE NEERKRKEEE  60
DQR                                                                63

SEQ ID NO: 114         moltype = AA  length = 57
FEATURE                Location/Qualifiers
REGION                 1..57
                       note = Synthetic: LEKTI Domain 11 (residues 701-757)
source                 1..57
                       mol_type = protein
                       organism = synthetic construct
SEQUENCE: 114
GNTQDECAEY REQMKNGRLS CTRESDPVRD ADGKSYNNQC TMCKAKLERE AERKNEY     57

SEQ ID NO: 115         moltype = AA  length = 63
FEATURE                Location/Qualifiers
REGION                 1..63
                       note = Synthetic: LEKTI Domain 12 (residues 768-830)
source                 1..63
                       mol_type = protein
                       organism = synthetic construct
SEQUENCE: 115
ESGKDTCDEF RSQMKNGKLI CTRESDPVRG PDGKTHGNKC TMCKEKLERE AAEKKKKEDE  60
DRS                                                                63

SEQ ID NO: 116         moltype = AA  length = 63
FEATURE                Location/Qualifiers
REGION                 1..63
                       note = Synthetic: LEKTI Domain 13 (residues 843-905)
source                 1..63
                       mol_type = protein
                       organism = synthetic construct
SEQUENCE: 116
NDKEDLCREF RSMQRNGKLI CTRENNPVRG PYGKMHINKC AMCQSIFDRE ANERKKKDEE  60
KSS                                                                63

SEQ ID NO: 117         moltype = AA  length = 62
FEATURE                Location/Qualifiers
REGION                 1..62
                       note = Synthetic: LEKTI Domain 14 (residues 910-970)
source                 1..62
                       mol_type = protein
                       organism = synthetic construct
SEQUENCE: 117
NNAKDECSEF RNYIRNNELI CPRENDPVHG ADGKFYTNKC YMCRAVFLTE ALERAKLQEK  60
PS                                                                 62

SEQ ID NO: 118         moltype = AA  length = 62
FEATURE                Location/Qualifiers
REGION                 1..62
                       note = Synthetic: LEKTI Domain 15 (residues 987-1048)
source                 1..62
                       mol_type = protein
                       organism = synthetic construct
SEQUENCE: 118
SLDSEMCKDY RVLPRIGYLC PKDLKPVCGD DGQTYNNPCM LCHENLIRQT NTHIRSTGKC  60
EE                                                                 62

SEQ ID NO: 119         moltype = DNA  length = 3192
FEATURE                Location/Qualifiers
misc_feature           1..3192
                       note = Synthetic: LEKTI Full length Nucleic acid sequence
```

```
source                 1..3192
                       mol_type = other DNA
                       organism = synthetic construct
SEQUENCE: 119
atgaagatag ccacagtgtc agtgcttctg cccttggctc tttgcctcat acaagatgct  60
gccagtaaga atgaagatca ggaaatgtgc catgaatttc aggcatttat gaaaaatgga  120
aaactgttct gtccccagga taagaaattt tttcaaagtc ttgatggaat aatgttcatc  180
aataaatgtg ccacgtgcaa aatgatactg gaaaaagaag caaaatcaca gaagagggcc  240
aggcatttag caagagctcc caaggctact gccccaacag agctgaattg tgatgatttt  300
aaaaaaggag aaagagatgg ggattttatc tgtcctgatt attatgaagc tgtttgtggc  360
acagatggga aaacatatga caacagatgt gcactgtgtg ctgagaatgc gaaaaccggg  420
tcccaaattg gtgtaaaaag tgaaggggaa tgtaagagca gtaatccaga gcaggatgta  480
tgcagtgctt ttcggccctt tgttagagat ggaagacttg gatgcacaag ggaaaatgat  540
cctgttcttg gtcctgatgg gaagacgcat ggcaataagt gtgcaatgtg tgctgagctg  600
tttttaaaag aagctgaaaa tgccaagcga gagggtgaaa ctagaattcg acgaaatgct  660
gaaaaggatt tttgcaagga atatgaaaaa caagtgagaa atggaaggct tttttgtaca  720
cgggagagtg atccagtccg tggccctgac ggcaggatgc atggcaacaa atgtgccctg  780
tgtgctgaaa ttttcaagca gcgtttttca gaggaaaaca gtaaaacaga tcaaaatttg  840
ggaaaagctg aagaaaaaac taaagttaaa agagaaattg tgaaactctg cagtcaatat  900
caaaatcagg caaagaatgg aatacttttc tgtaccagag aaaatgaccc tattcgtggt  960
ccagatggga aaatgcatgg caacttgtgt tccatgtgtc aagcctactt ccaagcagaa  1020
aatgaagaaa agaaaaaggc tgaagcacga gctagaaaca aaagagaatc tggaaaagca  1080
acctcatatg cagagctttg cagtgaatat cgaaagcttg tgaggaacgg aaaacttgct  1140
tgcaccagag agaacgatcc tatccagggc ccagatggga aagtgcatgg caacacctgc  1200
tccatgtgtg aggtcttctt ccaagcagaa gaagaagaaa agaaaaagaa ggaaggtaaa  1260
tcaagaaaca aaagacaatc taagagtaca gcttcctttg aggagttgtg tagtgaatac  1320
cgcaaatcca ggaaaaacgg acggcttttt tgcaccagag agaatgaccc catccagggc  1380
ccagatggaa aaatgcatgg caacacctgc tccatgtgtg aggccttctt tcaacaagaa  1440
gaaagagcaa gagcaaaggc taaaagagaa gctgcaaagg aaatctgcag tgaatttcgg  1500
gaccaagtga ggaatggaac acttatatgc accagggagc ataatcctgt ccgtggccca  1560
gatggcaaaa tgcatggaaa caagtgtgcc atgtgtgcca gtgtgttcaa acttgaagaa  1620
gaagagaaga aaaatgataa agaagaaaaa gggaaagtcg aggctgaaaa agttaagaga  1680
gaagcagttc aggagctgtg cagtgaatat cgtcattatg tgaggaatgg acgactcccc  1740
tgtaccagag agaatgatcc tattgagggt ctagatggga aaatccacgg caacacctgc  1800
tccatgtgtg aagccttctt ccagcaagaa gcaaaagaaa aagaaagagc tgaacccaga  1860
gcaaaagtca aaagagaagc tgaaaaggag acatgcgatg aatttcggag acttttgcaa  1920
aatggaaaac ttttctgcac aagagaaaat gatcctgtgc gtggcccaga tggcaagacc  1980
catggcaaca agtgtgccat gtgtaaggca gtcttccaga aagaaaatga ggaaagaaag  2040
aggaaagaag aggaagatca gagaaatgct gcaggacatg gttccagtgg tggtggagga  2100
ggaaacactc aggacgaatg tgctgagtat cgggaacaaa tgaaaaatgg aagactcagc  2160
tgtactcggg agagtgatcc tgtacgtgat gctgatggca aatcgtacaa caatcagtgt  2220
accatgtgta aagcaaaatt ggaaagagaa gcagagagaa aaaatgagta ttctcgctcc  2280
agatcaaatg ggactggatc agaatcaggg aaggatacat gtgatgagtt tagaagccaa  2340
atgaaaaatg gaaaactcat ctgcactcga gaaagtgacc ctgtccgggg tccagatggc  2400
aagacacatg gcaataagtg tactatgtgt aaggaaaaac tggaaaggga agcagctgaa  2460
aaaaaaaaga aagaggatga agacaggagc aatacaggag aaaggagcaa tacaggagaa  2520
aggagcaatg acaaagagga tctgtgtcgt gaatttcgaa gcatgcagag aaatggaaag  2580
cttatctgca ccagagaaaa taaccctgtt cgaggcccat atggcaagat gcacatcaat  2640
aaatgtgcta tgtgtcagag catctttgat cgagaagcta atgaaagaaa aaagaaagat  2700
gaagagaaat caagtagcaa gccctcaaat aatgcaaagg atgagtgcag tgaatttcga  2760
aactatataa ggaacaatga actcatctgc cctagagaga atgacccagt gcacggtgct  2820
gatggaaagt tctatacaaa caagtgctac atgtgcagag ctgtctttct aacagaagct  2880
ttggaaaggg caaagcttca agaaaagcca tcccatgtta gagcttctca agaggaagac  2940
agcccagact ctttcagttc tctggattct gagatgtgca aagactaccg agtattgccc  3000
aggataggtt atctttgtcc aaaggattta aagcctgtct gtggtgacga tggccaaacc  3060
tacaacaatc cttgcatgct ctgtcatgaa aacctgatac gccaaacaaa tacacacatc  3120
cgcagtacag ggaagtgtga ggagagcagc accccaggaa ccaccgcagc cagcatgccc  3180
ccgtctgacg aa                                                      3192

SEQ ID NO: 120         moltype = DNA  length = 326
FEATURE                Location/Qualifiers
misc_feature           1..326
                       note = Synthetic: PyxiE
source                 1..326
                       mol_type = other DNA
                       organism = synthetic construct
SEQUENCE: 120
acgattacag aatcaactat ctgcgtgatc atttaattga agcgcgcgaa gccattgcgg  60
acggcgttga attaatcgga tacacatcat gggggccaat tgaccttgtc agcgcatcta  120
ctgcggaaat gaaaaagcgc tacggcttca tttatgtaga ccgggacaat gaaggaaatg  180
gaacatttaa ccgcatcaag aaaaaaagct tcaactggta tcagcaggtt atcgccacaa  240
acggagagag tctctgacaa ttttttgaaa actcatgcgc ttcaattgac aataacgaaa  300
tgcaggcgga caataaaaga gaaagg                                       326

SEQ ID NO: 121         moltype = DNA  length = 24
FEATURE                Location/Qualifiers
misc_feature           1..24
                       note = Synthetic: RBSsod
source                 1..24
```

```
                        mol_type = other DNA
                        organism = synthetic construct
SEQUENCE: 121
ggtaccttag gaggatgatt attt                                          24

SEQ ID NO: 122          moltype = DNA  length = 87
FEATURE                 Location/Qualifiers
misc_feature            1..87
                        note = Synthetic: yfhK
source                  1..87
                        mol_type = other DNA
                        organism = synthetic construct
SEQUENCE: 122
atgaaaaaga aacaagtaat gctcgcttta acagctgccg caggactggg tttgacagca  60
cttcattccg ctcccgcagc aaaagct                                       87

SEQ ID NO: 123          moltype = DNA  length = 27
FEATURE                 Location/Qualifiers
misc_feature            1..27
                        note = Synthetic: Pro9
source                  1..27
                        mol_type = other DNA
                        organism = synthetic construct
SEQUENCE: 123
ttagaaattt catcaacatg tgatgca                                       27

SEQ ID NO: 124          moltype = DNA  length = 690
FEATURE                 Location/Qualifiers
misc_feature            1..690
                        note = Synthetic: PyxiE-RBSsod-SPyfhK-pro9-LEKTI-d6
source                  1..690
                        mol_type = other DNA
                        organism = synthetic construct
SEQUENCE: 124
acgattacag aatcaactat ctgcgtgatc atttaattga agcgcgcgaa gccattgcgg  60
acggcgttga attaatcgga tacacatcat gggggccaat tgaccttgtc agcgcatcta  120
ctgcggaaat gaaaaagcgc tacggcttca tttatgtaga ccgggacaat gaaggaaatg  180
gaacatttaa ccgcatcaag aaaaaaagct tcaactggta tcagcaggtt atcgccacaa  240
acggagagag tctctgacaa ttttttgaaa actcatgcgc ttcaattgac aataacgaaa  300
tgcaggcgga caataaaaga gaaaggtcga ctaccttagg aggatgatta tttatgaaaa  360
agaaacaagt aatgctcgct ttaacagctg ccgcaggact gggtttgaca gcacttcatt  420
ccgctcccgc agcaaaagct gccgaattct tagaaatttc atcaacatgt gatgcagaat  480
ctggtaaagc aacgagttac gctgaattgt gctcagaata ccgtaagtta gtcagaaacg  540
gaaagttggc gtgtactcgt gagaacgacc ctatccaggg accggacggc aaggtacatg  600
gaaatacttg cagtatgtgc gaggtgtttt tccaggcgga ggaagaagaa aagaagaaaa  660
aggagggcaa aagtcgaaat taatgaataa                                    690

SEQ ID NO: 125          moltype = AA  length = 13
FEATURE                 Location/Qualifiers
REGION                  1..13
                        note = Synthetic: cell penetrating sequence
source                  1..13
                        mol_type = protein
                        organism = synthetic construct
SEQUENCE: 125
GRKKRRQRRR PPQ                                                      13

SEQ ID NO: 126          moltype = AA  length = 27
FEATURE                 Location/Qualifiers
REGION                  1..27
                        note = Synthetic: cell penetrating sequence
source                  1..27
                        mol_type = protein
                        organism = synthetic construct
SEQUENCE: 126
GWTLNSAGYL LGKINLKALA ALAKKIL                                       27

SEQ ID NO: 127          moltype = DNA  length = 28
FEATURE                 Location/Qualifiers
misc_feature            1..28
                        note = Synthetic: GA-pJB-3'2-F
source                  1..28
                        mol_type = other DNA
                        organism = synthetic construct
SEQUENCE: 127
cggatcctac ccggatcgat cctctaga                                      28

SEQ ID NO: 128          moltype = DNA  length = 58
FEATURE                 Location/Qualifiers
```

```
misc_feature           1..58
                       note = Synthetic: 5  of SEagr-pJB-GA-F
source                 1..58
                       mol_type = other DNA
                       organism = synthetic construct
SEQUENCE: 128
ttcgagctcg cccgctaagc gctacccgcg agctgataaa aatcttaaag acagctct    58

SEQ ID NO: 129         moltype = DNA  length = 35
FEATURE                Location/Qualifiers
misc_feature           1..35
                       note = Synthetic: 5' of SE1634-GA-R
source                 1..35
                       mol_type = other DNA
                       organism = synthetic construct
SEQUENCE: 129
taatttttga atgagtctat tgtaactttt gtaac                             35

SEQ ID NO: 130         moltype = DNA  length = 44
FEATURE                Location/Qualifiers
misc_feature           1..44
                       note = Synthetic: 5' of SE1634-GA-d6-F
source                 1..44
                       mol_type = other DNA
                       organism = synthetic construct
SEQUENCE: 130
caatagactc attcaaaaat tcattaattt cgacttttgc cctc                   44

SEQ ID NO: 131         moltype = DNA  length = 46
FEATURE                Location/Qualifiers
misc_feature           1..46
                       note = Synthetic: PyxiE-GA-3'SE1634R
source                 1..46
                       mol_type = other DNA
                       organism = synthetic construct
SEQUENCE: 131
cgaaaggagt gaagttataa tgacgattac agaatcaact atctgc                 46

SEQ ID NO: 132         moltype = DNA  length = 30
FEATURE                Location/Qualifiers
misc_feature           1..30
                       note = Synthetic: 3' of SE1634-F
source                 1..30
                       mol_type = other DNA
                       organism = synthetic construct
SEQUENCE: 132
cattataact tcactccttt cgaattaagg                                   30

SEQ ID NO: 133         moltype = DNA  length = 52
FEATURE                Location/Qualifiers
misc_feature           1..52
                       note = Synthetic: 3' of SE1634-GA-R
source                 1..52
                       mol_type = other DNA
                       organism = synthetic construct
SEQUENCE: 133
cgatccgggt aggatccgct aagggttata tttactcgta tagtttagtc ag          52

SEQ ID NO: 134         moltype = DNA  length = 25
FEATURE                Location/Qualifiers
misc_feature           1..25
                       note = Synthetic: 5' outSEagr-F
source                 1..25
                       mol_type = other DNA
                       organism = synthetic construct
SEQUENCE: 134
cagaaatgtg gaataacggt tatgc                                        25

SEQ ID NO: 135         moltype = DNA  length = 22
FEATURE                Location/Qualifiers
misc_feature           1..22
                       note = Synthetic: 3' outSEagr
source                 1..22
                       mol_type = other DNA
                       organism = synthetic construct
SEQUENCE: 135
gcttcgactg aatctggtca ag                                           22
```

EXPRESSION OF THE HUMAN LEKTI GENE FROM THE CHROMOSOME OF *STAPHYLOCOCCUS ePIDERMIDIS*

RELATED APPLICATIONS

This application claims priority to U.S. Provisional Application No. 63/305,458, filed Feb. 1, 2022, the entire contents of which are incorporated herein by reference.

SEQUENCE LISTING

The instant application contains a Sequence Listing which has been submitted electronically in XML format and is hereby incorporated by reference in its entirety. Said XML copy, created on Jul. 17, 2023, is named 129062-01702_SL and is 171,386 bytes in size.

FIELD OF THE DISCLOSURE

The present disclosure relates to methods, kits, and compositions for treating or ameliorating the effects of a disease or disorder, e.g., a skin disease, using one or more recombinant microorganisms that are genetically modified to express one or more therapeutic polypeptides, e.g., LEKTI domains, on the skin of the subject.

BACKGROUND OF THE INVENTION

Proteases or proteolytic enzymes are essential in organisms, from bacteria and viruses to mammals. Proteases digest and degrade proteins by hydrolyzing peptide bonds. Serine proteases (EC. 3.4.21) have common features in the active site, primarily an active serine residue. There are two main types of serine proteases; the chymotrypsin/trypsin/elastase-like and subtilisin-like, which have an identical spatial arrangement of catalytic His, Asp, and Ser but in quite different protein scaffolds. Over twenty families (S1-S27) of serine proteases have been identified that are grouped into 6 clans on the basis of structural similarity and other functional evidence, SA, SB, SC, SE, SF & SG. The family of chymotrypsin/trypsin/elastase-like serine proteases have been subdivided into two classes. The "large" class (ca 230 residues) includes mostly mammalian enzymes such as trypsin, chymotrypsin, elastase, kallikrein, and thrombin. The "small" class (ca 190 residues) includes the bacterial enzymes. Examples of serine proteases include trypsin, tryptase, chymotrypsin, elastase, thrombin, plasmin, kallikrein, Complement Cl, acrosomal protease, lysosomal protease, cocoonase, a-lytic protease, protease A, protease B, serine carboxypeptidase, subtilisin, urokinase (uPA), Factor Vila, Factor IXa, and Factor Xa. The serine proteases have been investigated extensively for many years and are a major focus of research as a drug target due to their role in regulating a wide variety of physiological processes.

One branch of the family of serine protease inhibitors is that of the Kazal type (SPINK) gene that includes SPINK1, SPINK2, SPINK4, SPINK5, SPINK6, SPINK7, SPINK8, SPINK9, SPINK13 and SPINK14). The lymphoepithelial kazal-type inhibitor (LEKTI) is encoded by SPINK5 (Serine Proteinase Inhibitor Kazal type 5) (Magert et al. (1999) J Biol. Chem. 274; 21499-21502). The SPINK5 gene is located on chromosome 5q32 among a cluster of other SPINK genes (e.g., SPINK1, SPINK6, SPINK7, SPINK9 and SPINK13), and comprises 33 exons encoding 15 inhibitory domains separated by linker regions. SPINK5 has shown to be expressed in the skin, oral mucosa, tonsils, parathyroid gland, thymus, and lung (Magert et al., Int J Biochem Cell Biol. 2002; 34(6):573-6; Magert et al., Eur J Med Res. 2002; 7(2):49-56).

SPINK5 stands out among the other SPINK genes for the large number of inhibitory domains it encodes. The SPINK5 gene is transcribed into three different transcripts, resulting in three different LEKTI proteins that differ in the C-terminal region; i.e., a 145 kDa full length protein having inhibitory domains D1-D15, a 125 kDa (short) protein having inhibitory domains D1-D12, and a 148 kDa (long) protein having an extended linker region 13. LEKTI is expressed as high molecular mass precursors, which are rapidly processed into several proteolytic fragments secreted in the intercellular space (Bitoun et al. (2003) Hum. Mol. Genet. 12:2417-2430). The Kazal motif of LEKTI is defined by the presence of six cysteine residues positioned at specific distances to allow formation of three disulfide bonds in a 1-5, 2-4, and 3-6 pattern. Two of the domains of LEKTI (D2 and D5) form this six cysteine motif, while other domains share four cysteine residues, which produce a rigid inhibitory loop believed to mimic the substrate of target proteases and inactivate the target protease catalytic site. The LEKTI protein requires proteolytic cleavage for activation of its inhibitory function against many proteases. The full length protein is cleaved into domains D1-D5 and D6-D15. The D6-D15 domains are then further cleaved in multiple steps into D6-D9 and D10-D15, →D6 and D7-D9→D7 and D8-D9→D8. This process results in LEKTI proteins comprising between one and six inhibitory domains, with each protein having different protease targets. For example, it has been shown that LEKTI fragments can efficiently and specifically inhibit the epidermal kallikrein (KLK) 5, KLK7, and KLK14 (DeRaison et al. (2007) Mol. Biol. Cell. 18:3607-3619).

A number of current limitations exist in the disease, e.g., skin disease or disorder. Many treatments, such as topical corticosteroids or biologics, do not treat the underlying issues of deficient intrinsic protein in the epidermis or imbalances in the microbial diversity in the skin. While recombinant proteins represent a promising group of therapeutic agents in the treatment of skin disease, several problems accompany their use in the context of the skin.

Traditional methods purify and concentrate recombinant proteins that are extracted from bacterial systems, and then incorporate such preparations into a delivery system. The purification of recombinant proteins is often a very costly method of obtaining protein. Moreover, a number of problems are associated with these traditional methods, including proteolytic degradation, inefficient delivery, and the need for repeated application overtime to achieve therapeutic effect.

In view of the foregoing, there is a need for novel therapeutic agents for treatment of diseases or disorders in a subject in thereof. The present application is directed to meeting these and other needs.

SUMMARY OF THE INVENTION

According to one aspect, the present disclosure provides a recombinant microorganism capable of secreting one or more therapeutic polypeptide, wherein the recombinant organism comprises: (i) a first coding sequence comprising a nucleic acid sequence encoding one or more therapeutic polypeptide; (ii) a second coding sequence comprising a nucleic acid sequence encoding one or more secretion sequences that are not associated with the one or more therapeutic polypeptide in nature; and (iii) a third coding sequence comprising a pro-peptide, wherein the first coding sequence, second coding sequence, and third coding sequence are in-frame, wherein the one or more therapeutic polypeptides are encoded by one or more SPINK genes, or one or more protein domains thereof.

According to some embodiments, the first coding sequence, the second coding sequence, and the third coding sequence are chromosomally integrated.

According to some embodiments, the first coding sequence, the second coding sequence, and the third coding sequence are chromosomally integrated into the hld gene.

According to some embodiments, the recombinant microorganism is attenuated by auxotrophy.

According to some embodiments, the recombinant microorganism is a D-alanine auxotroph.

According to some embodiments, the expression of the first coding sequence, the second coding sequence, and the third coding sequence is operable linked to a promoter.

According to some embodiments, the promoter is P3.

According to some embodiments, the recombinant microorganism further comprises wherein the expression of the first coding sequence, second coding sequence and third coding sequence is under the control of a promoter PyxiE. According to some embodiments, the PyxiE comprises SEQ ID NO: 120.

According to some embodiments, the secretion peptide is *Bacillus subtilis* yfhK gene. According to some embodiments, the secretion peptide comprises SEQ ID NO: 122.

According to some embodiments, the pro-peptide comprises SEQ ID NO: 123.

According to some embodiments, the recombinant microorganism is bacteria. According to some embodiments, the microorganism is selected from the group consisting of *Moraxella, Corynebacteria, Pasteurella, Haemophilus, Streptococcus*, or *Staphylococcus*. According to some embodiments, the recombinant microorganism is *Staphylococcus epidermidis.*

According to some embodiments, the one or more SPINK genes are selected form the group consisting of SPINK1, SPINK2, SPINK4, SPINK5, SPINK6, SPINK7, SPINK8, SPINK9, SPINK13, and SPINK14. According to some embodiments, the one or more SPINK gene is SPINK5. According to some embodiments, the one or more SPINK gene encodes a LEKTI protein, or one or more protein domains thereof.

According to some embodiments, the recombinant microorganism secretes the one or more therapeutic polypeptide.

According to some embodiments, the LEKTI protein domain is selected from the group consisting of D1, D2, D3, D4, D5, D6, D7, D8, D9, D10, D11, D12, D13, D14, and D15.

According to some embodiments, the LEKTI protein domain is D6.

According to another aspect, the present disclosure provides a method of producing a live biotherapeutic composition, the method comprising: transfecting a cell with a nucleic acid sequence comprising (i) one or more LEKTI protein domains, (ii) a secretion peptide that is not associated with the one or more therapeutic polypeptide in nature, (iii) a pro-peptide, and (iv) a promoter; and integrating the nucleic acid sequence into the chromosome of the cell; and obtaining the live biotherapeutic.

According to some embodiments, the secretion peptide is selected from *Bacillus subtilis* yfhK gene. According to some embodiments, the secretion peptide comprises SEQ ID NO: 122.

According to some embodiments, the pro-peptide comprises SEQ ID NO: 123.

According to some embodiments, the nucleic acid sequence is integrated into the hld gene.

According to some embodiments, the promoter is PyxiE. According to some embodiments, PyxiE comprises SEQ ID NO: 120.

According to some embodiments, the nucleic acid sequence is under the control of an endogenous promoter.

According to some embodiments, the endogenous promoter is P3.

According to some embodiments, the arrangement of the LEKTI protein domain, secretion peptide, and pro-peptide are in-frame.

According to some embodiments, the recombinant microorganism is bacteria. According to some embodiments, the recombinant microorganism is selected from the group consisting of *Moraxella, Corynebacteria, Pasteurella, Haemophilus, Streptococcus*, or *Staphylococcus*. According to some embodiments, the recombinant microorganism is *Staphylococcus epidermidis.*

According to some embodiments, the recombinant microorganism secretes the one or more LEKTI protein domain, or variants thereof.

According to another aspect, the present disclosure provides a composition obtained by any one of the methods disclosed herein.

According to some embodiments, the composition comprises a pharmaceutically acceptable carrier, wherein the pharmaceutically acceptable carrier is selected from the group consisting of an aqueous solution, an emulsion, a cream, a lotion, a gel, and an ointment.

According to another aspect, the present disclosure provides a live biotherapeutic composition comprising a recombinant microorganism, wherein the recombinant microorganism comprises: a nucleic acid sequence comprising (i) one or more LEKTI protein domains, (ii) one or more secretion peptides, (iii) a pro-peptide, and (iv) a promoter, wherein the recombinant microorganism is capable of secreting the one or more LEKTI protein domains, or a variant thereof.

According to some embodiments, the nucleic acid sequence is integrated into the chromosome of the cell.

According to some embodiments, the nucleic acid sequence is integrated into the hld gene.

According to some embodiments, the secretion peptide is from *Bacillus subtilis* yfhK gene. According to some embodiments, the secretion peptide comprises SEQ ID NO: 122.

According to some embodiments, the pro-peptide comprises SEQ ID NO: 123.

According to some embodiments, the promoter is PyxiE. According to some embodiments, PyxiE comprises SEQ ID NO: 120.

According to some embodiments, the one or more LEKTI protein domains, one or more secretion peptides, and propeptide are under the control of an endogenous promoter.

According to some embodiments, the endogenous promoter is P3.

According to some embodiments, the arrangement of the one or more LEKTI protein domains, one or more secretion peptides, and pro-peptide are in-frame.

According to some embodiments, the recombinant microorganism is bacteria. According to some embodiments, the recombinant microorganism is selected from the group consisting of *Moraxella, Corynebacteria, Pasteurella, Haemophilus, Streptococcus*, or *Staphylococcus*. According to some embodiments, the recombinant microorganism is *Staphylococcus epidermidis.*

According to some embodiments, the composition comprises a pharmaceutically acceptable carrier, wherein the pharmaceutically acceptable carrier is selected from the group consisting of an aqueous solution, an emulsion, a cream, a lotion, a gel, and an ointment.

According to another aspect, the present disclosure provides a kit comprising any one of the compositions disclosed herein and instructions for use.

According to another aspect, the present disclosure provides a method of treating a disease or disorder comprising administering to a subject in need thereof any one of the compositions disclosed herein.

According to some embodiments, the disease or disorder is selected from a skin disease, a disease or disorder associated with pain, cancer, and a viral infection.

According to some embodiments, the skin disease is selected from the group consisting of pruritus, rosacea, psoriasis, atopic dermatitis, Ichthyosis vulgaris, and Netherton Syndrome.

According to some embodiments, the disease or disorder associated with pain is selected from the group consisting of acute pain, chronic pain, nociceptive pain, neuropathic pain, traumatic pain, inflammatory pain, post-operative incision pain, pain associated with cancer, fracture pain, osteoporotic pain, bone cancer pain, and gout joint pain.

According to some embodiments, the cancer is selected from the group consisting of malignant melanoma, colon cancer, breast cancer, lung cancer, ovarian cancer, gastric cancer, oral tongue squamous cell carcinoma, squamous cell cancer, prostate cancer, pancreatic cancer, liver cancer, kidney cancer, bladder cancer, cervical cancer, endometrial cancer, gallbladder cancer, brain cancer and oral cancer.

According to some embodiments, the viral infection is selected from a group consisting of a respiratory infection, dermal infection, and a viral infection that causes cancer in a subject.

BRIEF DESCRIPTION OF THE DRAWINGS

FIG. 1B depicts plasmid pLEKTI-27a-d6 in *S. epidermidis* strain 27a.

FIG. 4A depicts a graph comparing expression of LEKTI during logarithmic and stationary growth phases in *S. epidermidis* strain 27a.

DETAILED DESCRIPTION OF THE INVENTION

Figure 1A:
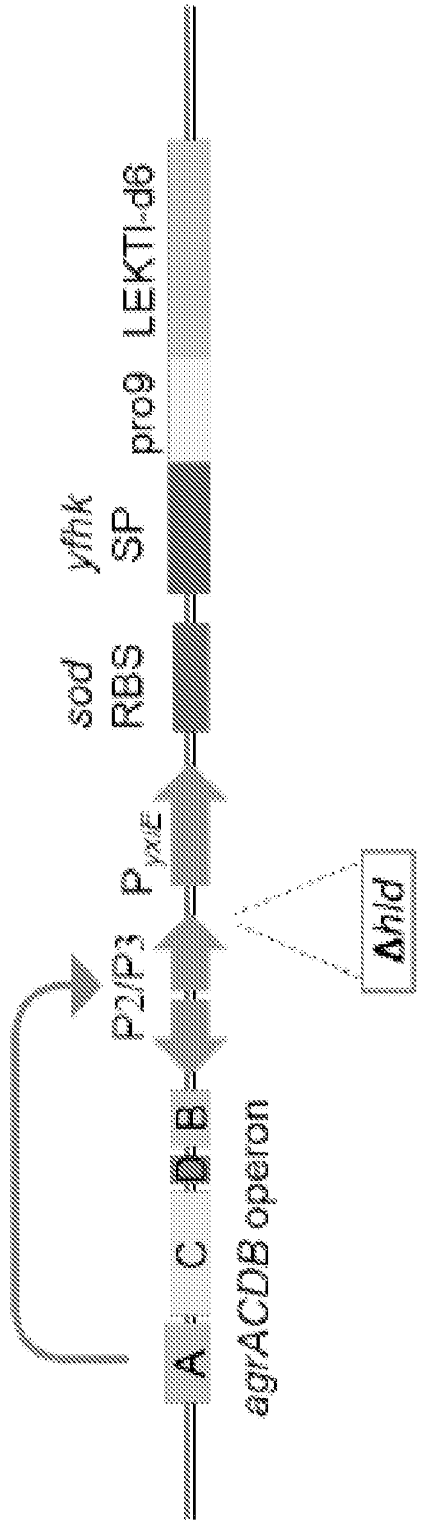
FIG. 1A depicts chromosomal hLEKTI-d6 expression cassette.

One aspect of the present disclosure provides skin-colonizing bacteria, e.g., *Staphylococcus epidermidis*, that are genetically altered to express chromosomally integrated recombinant proteins to treat or ameliorate skin disease. The genetically altered protein-producing bacteria are able to treat skin disease by expressing and, optionally, secreting a therapeutic protein that treats the underlying cause of the skin disease or its symptoms. According to some embodiments, the therapeutic protein comprises one or more LEKTI domains that are effective to inhibit serine proteases within or on the skin of a mammal. According to some embodiments, the recombinant LEKTI domains compensate for the defective endogenous LEKTI protein naturally produced by the skin in the mammal. According to some embodiments, the genetically altered bacteria are able to self-replicate while retaining the ability to produce the recombinant protein, thereby providing a continuous supply of therapeutic agent.

According to some embodiments, the disclosure provides a composition for the treatment of a skin disease comprising a microbe genetically modified to express and provide one or more LEKTI protein domains onto the skin of a mammal, wherein the LEKTI protein domains are effective to penetrate one or more layers of the mammal's skin and effective to inhibit serine protease activity of at least one serine protease in or on the mammal's skin.

According to some embodiments, the disclosure provides a recombinant *Staphylococcus epidermidis* strain containing a DNA cassette in its chromosome which expresses a secreted form of the domain 6 of LEKTI protein (hLEKTI-d6) of the human SPINK5 gene. The host strain harboring this expression cassette in its chromosome is *S. epidermidis* strain $SE_{\Delta\Delta\Delta}$, a strain containing deletions of three genes involved in the biosynthesis of the essential amino acid, D-alanine [two alanine racemase genes (alr1 and alr2) and the D-alanine aminotransferase gene (dat)], making the strain auxotrophic to this amino acid.

According to some embodiments, the chromosomal hLEKTI-d6 construct strain possesses several differentiating properties as compared to another strain, *S. epidermidis* 27a, which is *S. epidermidis* $SE_{\Delta\Delta\Delta}$ expressing secreted hLEKTI-d6 protein from a plasmid construct that also contains an alrA gene complementing D-alanine auxotrophy. These properties include: 1) retention of the D-alanine auxotrophy of $SE_{\Delta\Delta\Delta}$, providing a measure of growth control using D-alanine supplementation; 2) an unexpected enhanced production of secreted hLEKTI-d6 protein, presumably influenced by the genetic environment at the chromosomal site of integration, enhanced levels of secreted hLEKTI-d6 protein may be due to a synergy of promoter combinations driving hLEKTI-d6 gene expression (1; 2), activation of transcription triggered by quorum sensing in dense cultures (3; 4), and/or unique DNA or RNA structure associated with regulation of the delta-toxin gene, hld (4); and 3) potential enhanced stability of the expression cassette, and reduced potential for lateral transmission to commensal flora, due to the chromosomally integrated nature of the expression cassette vs. being carried on an extrachromosomal genetic element (plasmid).

As used herein the term "skin disease" and grammatical variations thereof means a skin state or condition that is generally undesirable or deleterious compared to the normal or baseline condition of human skin. Examples of abnormal skin conditions include, without limitation, Netherton Syndrome, psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and molecules used in washing detergents and sodium lauryl sulfate), thinning skin (e.g. skin from the elderly and children), bullous pemphigoid, pemphigus vulgaris, impetigo, vitiligio, baldness, and hirsutism.

As used herein, the term "genetically modified" and grammatical variations thereof are used to describe a microbial organism (e.g., bacteria) that has been genetically modified or engineered by the introduction of DNA prepared outside the microbe. For example, the introduction of plasmid DNA containing new genes into bacteria will allow the bacteria to express those genes. Alternatively, the DNA containing new genes can be introduced to the bacteria and then integrated into the bacteria's genome, where the bacteria will express those genes.

As used herein, the term "microorganism" or "recombinant microorganism" refers to a microorganism, e.g., bacteria cell, that has been genetically modifies form its native state. Thus, a "recombinant bacterial cell" or "recombinant bacteria" refers to a bacterial cell or a bacteria that have been genetically modified form their native state. For instance, a recombinant bacterial cell may have nucleotide insertions, nucleotide deletions, nucleotide rearrangements, and nucleotide modifications introduced into their DNA. These genetic modifications may be present in the chromosome of the bacteria or bacterial cell. Recombinant bacterial cells may comprise exogenous nucleotide sequences stably incorporated into their chromosome.

As used herein, the terms "treat," "treating," "treatment" and grammatical variations thereof mean providing to a subject a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

In the present invention, the subject may be a mammal. As used herein, a "mammal" and grammatical variations thereof means any category of mammal. In the present invention, mammals include, for example, humans, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc. Preferably, the mammal is a human.

As used herein, the term "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a composition according to the invention will be that amount of the composition, which is the lowest dose effective to produce the desired effect. The effective dose of a composition of the present invention may be administered as two, three, four, five, six or more sub-doses, administered separately at appropriate intervals throughout the day.

Microbial compositions: According to some embodiments, the disclosure provides microbial compositions comprising one or more of a wide range of bacteria suitable for use on a mammal's skin. Examples include, but are not limited to, non-pathogenic and commensal bacteria. Bacteria suitable for use in the present invention include, but are not limited to, *Bifidobacterium, Brevibacterium, Propionibacterium, Lactococcus, Streptococcus, Staphylococcus* (e.g., *S. epidermidis* and/or *S. hominis*), *Lactobacillus* (e.g., *L. acidophilus*), *Pediococcus, Leuconostoc*, or *Oenococcus*. According to some embodiments, microbial compositions comprise one or more of *Staphylococcus* warneri, *Streptococcus pyogenes, Streptococcus mitis, Propionibacterium acnes, Corynebacterium* spp., *Acinetobacter johnsonii, Pseudomonas aeruginosa*. According to some embodiments, other related or similar species found on the skin are used.

Certain embodiments involve the use of bacterium *Staphylococcus epidermidis*. According to some embodiments, the strain of *S. epidermidis* to be used is incapable of producing biofilms. An example of this is *S. epidermidis* strain ATCC 12228 or NRRL B-4268.

According to some embodiments, the recombinant microbe is adapted to live indefinitely or for a controlled duration on the surface of the mammal's skin to provide a continuous supply of LEKTI protein domains. In some embodiments, the recombinant microbe lives alongside commensal microorganisms naturally occurring on the mammal's skin. In some embodiments, the recombinant microbe lives to the exclusion of commensal microorganisms that naturally occur on the mammal's skin. According to some embodiments, the recombinant microbe is adapted to multiply on the skin of the mammal. In other embodiments, the recombinant microbe is no longer alive, but contains effective amounts of a therapeutic polypeptide, e.g., LEKTI or therapeutically effective domain(s) thereof. Such cells may be intact or not depending upon the particulars of delivering the therapeutic peptide (or domain(s) thereof) to the target site.

As used herein, the term "recombinant" and grammatical variations thereof means relating to or denoting an organism, protein, or genetic material formed by or using recombined DNA comprising DNA pieces from different sources or from different parts of the same source. For example, the term "recombinant DNA" means a DNA molecule formed through recombination methods to splice fragments of DNA from a different source or from different parts of the same source. In some embodiments, two or more different sources of DNA are cleaved using restriction enzymes and joined together using ligases. As another example, the term "recombinant protein" or "recombinant domains" and grammatical variations thereof means a protein molecule formed through recombination methods originating from spliced fragments of DNA from a different source or from different parts of the same source. As another example, the term "recombinant microbe" or "recombinant bacteria" and grammatical variations thereof mean a microbe/bacteria that comprises one or more recombinant DNA/protein molecules.

LEKTI gene: According to some embodiments, the recombinant microbe is engineered to express a mammalian gene encoding LEKTI protein. The LEKTI gene can be obtained from any mammal, such as mouse, rat, rabbit, goat, sheep, horse, cow, dog, primate, or human gene sequences. According to some embodiments, the LEKTI gene sequence is a human gene sequence. According to some embodiments, the recombinant microbe is engineered to comprise a fragment of the LEKTI gene.

According to some embodiments, the recombinant protein expressed by the engineered microbe comprises one or more protease inhibitory domains of the LEKTI protein. Some non-limiting examples include one or more of domains D1, D2, D3, D4, D5, D6, D7, D8, D9, D10, D11, D12, D13, D14, and D15. According to some embodiments, the recombinant protein expressed by the engineered microbe comprises LEKTI inhibitory domain 6 or domains D8 to D11.

According to some embodiments, the recombinant protein expressed by the engineered microbe comprises LEKTI D8-11. According to some embodiments, the recombinant protein expressed by the engineered microbe comprises LEKTI-D6. According to some embodiments, one or more fragments of LEKTI are expressed by the engineered microbe. In one embodiment, the fragment comprises one or more LEKTI domains. In a specific embodiment, the LEKTI domain is Domain 6.

The present disclosure also relates to allelic variants of LEKTI, or portions thereof (one or more of domains D1, D2, D3, D4, D5, D6, D7, D8, D9, D10, D11, D12, D13, D14, and D15), as well as synthetic or mutated genes of SPINK (e.g., SPINK5) that have been modified to change, for example, the expression or activity of the recombinant protein. It is also noted that degeneracy of the nucleic acid code can be considered variations in the nucleotide sequences that encode the same amino acid residues. Accordingly, the disclosure includes nucleic acid residues that are able to hybridize under moderately stringent conditions. One skilled in the art can determine effective combinations of salt and temperature to constitute a moderately stringent hybridization condition. It is also envisioned that orthologs of LEKTI are present in other species, for example, dog, sheep, rat, hamster, chicken and pig. Therefore in another embodiment of the present invention relates to SPINK (e.g., SPINK5) nucleic acids that encode polypeptides having at least about 70% to 80% identity, preferably 90% to 95% identity, more preferably 98% to 99% identity to LEKTI set forth in SEQ ID NO: 103 or portions thereof (one or more of domains D1, D2, D3, D4, D5, D6, D7, D8, D9, D10, D11, D12, D13, D14, and D15).

According to some embodiments, the LEKTI domains are selected from the non-limiting examples below, Tables 1 and 2.

TABLE 1

LEKTI Amino Acid sequences

| LEKTI Sequence | Amino Acid sequence | SEQ ID NO: |
|---|---|---|
| LEKTI amino acid sequence Residues 1-1064 | MKIATVSVLLPLALCLIQDAASKNEDQEMCHEFQAFMKNGK LFCPQDKKFFQSLDGIMFINKCATCKMILEKEAKSQKRARHL ARAPKATAPTELNCDDFKKGERDGDFICPDYYEAVCGTDGK TYDNRCALCAENAKTGSQIGVKSEGECKSSNPEQDVCSAFRP FVRDGRLGCTRENDPVLGPDGKTHGNKCAMCAELFLKEAE NAKREGETRIRRNAEKDFCKEYEKQVRNGRLFCTRESDPVR GPDGRMHGNKCALCAEIFKQRFSEENSKTDQNLGKAEEKTK VKREIVKLCSQYQNQAKNGILFCTRENDPIRGPDGKMHGNL CSMCQAYFQAENEEKKKAEARARNKRESGKATSYAELCSEY RKLVRNGKLACTRENDPIQGPDGKVHGNTCSMCEVFFQAEE EEKKKKEGKSRNKRQSKSTASFEELCSEYRKSRKNGRLFCTR ENDPIQGPDGKMHGNTCSMCEAFFQQEERARAKAKREAAK EICSEFRDQVRNGTLICTREHNPVRGPDGKMHGNKCAMCAS VFKLEEEEKKNDKEEKGKVEAEKVKREAVQELCSEYRHYVR NGRLPCTRENDPIEGLDGKIHGNTCSMCEAFFQQEAKEKERA EPRAKVKREAEKETCDEFRRLLQNGKLFCTRENDPVRGPDG KTHGNKCAMCKAVFQKENEERKRKEEEDQRNAAGHGSSGG GGGNTQDECAEYREQMKNGRLSCTRESDPVRDADGKSYNN QCTMCKAKLEREAERKNEYSRSRSNGTGSESGKDTCDEFRS QMKNGKLICTRESDPVRGPDGKTHGNKCTMCKEKLEREAAE KKKKEDEDRSNTGERSNTGERSNDKEDLCREFRSMQRNGKL ICTRENNPVRGPYGKMHINKCAMCQSIFDREANERKKKDEE KSSSKPSNNAKDECSEFRNYIRNNELICPRENDPVHGADGKF YTNKCYMCRAVFLTEALERAKLQEKPSHVRASQEEDSPDSFS SLDSEMCKDYRVLPRIGYLCPKDLKPVCGDDGQTYNNPCML CHENLIRQTNTHIRSTGKCEESSTPGTTAASMPPSDE | 103 |
| LEKTI Domain 1 (residues 23-77) | KNEDQEMCHEFQAFMKNGKLFCPQDKKFFQSLDGIMFINKC ATCKMILEKEAKSQ | 104 |
| LEKTI Domain 2 (residues 91-153) | APTELNCDDFKKGERDGDFICPDYYEAVCGTDGKTYDNRCA LCAENAKTGSQIGVKSEGECKS | 105 |
| LEKTI Domain 3 (residues 155-216 | NPEQDVCSAFRPFVRDGRLGCTRENDPVLGPDGKTHGNKCA MCAELFLKEAENAKREGETRI | 106 |
| LEKTI Domain 4 (residues 219-285) | NAEKDFCKEYEKQVRNGRLFCTRESDPVRGPDGRMHGNKC ALCAEIFKQRFSEENSKTDQNLGKAEE | 107 |

TABLE 1-continued

LEKTI Amino Acid sequences

| LEKTI Sequence | Amino Acid sequence | SEQ ID NO: |
|---|---|---|
| LEKTI_Domain 5 (residues 291-352) | REIVKLCSQYQNQAKNGILFCTRENDPIRGPDGKMHGNLCS MCQAYFQAENEEKKKAEARAR | 108 |
| LEKTI_Domain 6 (residues 356-423) | ESGKATSYAELCSEYRKLVRNGKLACTRENDPIQGPDGKVH GNTCSMCEVFFQAEEEEKKKKEGKSRN | 109 |
| LEKTI Domain 7 (residues 431-489) | ASFEELCSEYRKSRKNGRLFCTRENDPIQGPDGKMHGNTCS MCEAFFQQEERARAKAKR | 110 |
| LEKTI Domain 8 (residues 490-550) | EAAKEICSEFRDQVRNGTLICTREHNPVRGPDGKMHGNKCA MCASVFKLEEEEKKNDKEEKG | 111 |
| LEKTI Domain 9 (residues 561-622) | EAVQELCSEYRHYVRNGRLPCTRENDPIEGLDGKIHGNTCSM CEAFFQQEAKEKERAEPRAK | 112 |
| LEKTI Domain 10 (residues 626-688) | EAEKETCDEFRRLLQNGKLFCTRENDPVRGPDGKTHGNKCA MCKAVFQKENEERKRKEEEDQR | 113 |
| LEKTI Domain 11 (residues 701-757) | GNTQDECAEYREQMKNGRLSCTRESDPVRDADGKSYNNQC TMCKAKLEREAERKNEY | 114 |
| LEKTI Domain 12 (residues 768-830) | ESGKDTCDEFRSQMKNGKLICTRESDPVRGPDGKTHGNKCT MCKEKLEREAAEKKKKEDEDRS | 115 |
| LEKTI Domain 13 (residues 843-905) | NDKEDLCREFRSMQRNGKLICTRENNPVRGPYGKMHINKCA MCQSIFDREANERKKKDEEKSS | 116 |
| LEKTI Domain 14 (residues 910-970) | NNAKDECSEFRNYIRNNELICPRENDPVHGADGKFYTNKCY MCRAVFLTEALERAKLQEKPS | 117 |
| LEKTI Domain 15 (residues 987-1048) | SLDSEMCKDYRVLPRIGYLCPKDLKPVCGDDGQTYNNPCML CHENLIRQTNTHIRSTGKCEE | 118 |

TABLE 2

LEKTI Full Length Nucleotide Sequence

LEKTI Full length Nucleic acid sequence (SEQ ID NO: 119)

ATGAAGATAGCCACAGTGTCAGTGCTTCTGCCCTTGGCTCTTTGCC
TCATACAAGATGCTGCCAGTAAGAATGAAGATCAGGAAATGTGCC
ATGAATTTCAGGCATTTATGAAAAATGGAAAACTGTTCTGTCCCC
AGGATAAGAAATTTTTTCAAAGTCTTGATGGAATAATGTTCATCA
ATAAATGTGCCACGTGCAAAATGATACTGGAAAAAGAAGCAAAAT
CACAGAAGAGGGCCAGGCATTTAGCAAGAGCTCCCAAGGCTACTG
CCCCAACAGAGCTGAATTGTGATGATTTTAAAAAAGGAGAAAGAG
ATGGGGATTTTATCTGTCCTGATTATTATGAAGCTGTTTGTGGCA
CAGATGGGAAAACATATGACAACAGATGTGCACTGTGTGCTGAGA
ATGCGAAAACCGGGTCCCAAATTGGTGTAAAAAGTGAAGGGGAAT
GTAAGAGCAGTAATCCAGAGCAGGATGTATGCAGTGCTTTTCGGC
CCTTTGTTAGAGATGGAAGACTTGGATGCACAAGGGAAAATGATC
CTGTTCTTGGTCCTGATGGGAAGACGCATGGCAATAAGTGTGCAA
TGTGTGCTGAGCTGTTTTTAAAAGAAGCTGAAAATGCCAAGCGAG
AGGGTGAAACTAGAATTCGACGAAATGCTGAAAAGGATTTTTGCA
AGGAATATGAAAAACAAGTGAGAAATGGAAGGCTTTTTTGTACAC
GGGAGAGTGATCCAGTCCGTGGCCCTGACGGCAGGATGCATGGCA
ACAAATGTGCCCTGTGTGCTGAAATTTTCAAGCAGCGTTTTTCAG
AGGAAAACAGTAAAACAGATCAAAATTTGGGAAAAGCTGAAGAAA
AAACTAAAGTTAAAAGAGAAATTGTGAAACTCTGCAGTCAATATC
AAAATCAGGCAAAGAATGGAATACTTTTCTGTACCAGAGAAAATG
ACCCTATTCGTGGTCCAGATGGGAAAATGCATGGCAACTTGTGTT
CCATGTGTCAAGCCTACTTCCAAGCAGAAAATGAAGAAAAGAAAA

TABLE 2-continued

LEKTI Full Length Nucleotide Sequence

AGGCTGAAGCACGAGCTAGAAACAAAAGAGAATCTGGAAAAGCAA
CCTCATATGCAGAGCTTTGCAGTGAATATCGAAAGCTTGTGAGGA
ACGGAAAACTTGCTTGCACCAGAGAGAACGATCCTATCCAGGGCC
CAGATGGGAAAGTGCATGGCAACACCTGCTCCATGTGTGAGGTCT
TCTTCCAAGCAGAAGAAGAAGAAAAGAAAAAGAAGGAAGGTAAAT
CAAGAAACAAAAGACAATCTAAGAGTACAGCTTCCTTTGAGGAGT
TGTGTAGTGAATACCGCAAATCCAGGAAAAACGGACGGCTTTTTT
GCACCAGAGAGAATGACCCCATCCAGGGCCCAGATGGAAAAATGC
ATGGCAACACCTGCTCCATGTGTGAGGCCTTCTTTCAACAAGAAG
AAAGAGCAAGAGCAAAGGCTAAAAGAGAAGCTGCAAAGGAAATCT
GCAGTGAATTTCGGGACCAAGTGAGGAATGGAACACTTATATGCA
CCAGGGAGCATAATCCTGTCCGTGGCCCAGATGGCAAAATGCATG
GAAACAAGTGTGCCATGTGTGCCAGTGTGTTCAAACTTGAAGAAG
AAGAGAAGAAAAATGATAAAGAAGAAAAAGGGAAAGTCGAGGCTG
AAAAAGTTAAGAGAGAAGCAGTTCAGGAGCTGTGCAGTGAATATC
GTCATTATGTGAGGAATGGACGACTCCCCTGTACCAGAGAGAATG
ATCCTATTGAGGGTCTAGATGGGAAAATCCACGGCAACACCTGCT
CCATGTGTGAAGCCTTCTTCCAGCAAGAAGCAAAAGAAAAAGAAA
GAGCTGAACCCAGAGCAAAAGTCAAAAGAGAAGCTGAAAAGGAGA
CATGCGATGAATTTCGGAGACTTTTGCAAAATGGAAAACTTTTCT
GCACAAGAGAAAATGATCCTGTGCGTGGCCCAGATGGCAAGACCC
ATGGCAACAAGTGTGCCATGTGTAAGGCAGTCTTCCAGAAAGAAA
ATGAGGAAAGAAAGAGGAAAGAAGAGGAAGATCAGAGAAATGCTG
CAGGACATGGTTCCAGTGGTGGTGGAGGAGGAAACACTCAGGACG
AATGTGCTGAGTATCGGGAACAAATGAAAAATGGAAGACTCAGCT

TABLE 2-continued

| LEKTI Full Length Nucleotide Sequence |
|---|
| GTACTCGGGAGAGTGATCCTGTACGTGATGCTGATGGCAAATCGT<br>ACAACAATCAGTGTACCATGTGTAAAGCAAAATTGGAAAGAGAAG<br>CAGAGAGAAAAAATGAGTATTCTCGCTCCAGATCAAATGGGACTG<br>GATCAGAATCAGGGAAGGATACATGTGATGAGTTTAGAAGCCAAA<br>TGAAAAATGGAAAACTCATCTGCACTCGAGAAAGTGACCCTGTCC<br>GGGGTCCAGATGGCAAGACACATGGCAATAAGTGTACTATGTGTA<br>AGGAAAAACTGGAAAGGGAAGCAGCTGAAAAAAAAAAGAAAGAGG<br>ATGAAGACAGGAGCAATACAGGAGAAAGGAGCAATACAGGAGAAA<br>GGAGCAATGACAAAGAGGATCTGTGTCGTGAATTTCGAAGCATGC<br>AGAGAAATGGAAAGCTTATCTGCACCAGAGAAAATAACCCTGTTC<br>GAGGCCCATATGGCAAGATGCACATCAATAAATGTGCTATGTGTC<br>AGAGCATCTTTGATCGAGAAGCTAATGAAAGAAAAAAGAAAGATG<br>AAGAGAAATCAAGTAGCAAGCCCTCAAATAATGCAAAGGATGAGT<br>GCAGTGAATTTCGAAACTATATAAGGAACAATGAACTCATCTGCC<br>CTAGAGAGAATGACCCAGTGCACGGTGCTGATGGAAAGTTCTATA<br>CAAACAAGTGCTACATGTGCAGAGCTGTCTTTCTAACAGAAGCTT<br>TGGAAAGGGCAAAGCTTCAAGAAAAGCCATCCCATGTTAGAGCTT<br>CTCAAGAGGAAGACAGCCCAGACTCTTTCAGTTCTCTGGATTCTG<br>AGATGTGCAAAGACTACCGAGTATTGCCCAGGATAGGTTATCTTT<br>GTCCAAAGGATTTAAAGCCTGTCTGTGGTGACGATGGCCAAACCT<br>ACAACAATCCTTGCATGCTCTGTCATGAAAACCTGATACGCCAAA<br>CAAATACACACATCCGCAGTACAGGGAAGTGTGAGGAGAGCAGCA<br>CCCCAGGAACCACCGCAGCCAGCATGCCCCCGTCTGACGAA |

According to some embodiments, the recombinant microbe comprises a sequence as disclosed herein that has at least about 75% identity, or 80% identity, or 85% identity, or 90% identity, or 95% identity to any one or more of the SEQ ID NOS listed herein. As used herein, the term "identity" and grammatical versions thereof means the extent to which two nucleotide or amino acid sequences have the same residues at the same positions in an alignment. Percent (%) identity is calculated by multiplying the number of matches in a sequence alignment by 100 and dividing by the length of the aligned region, including internal gaps.

According to some embodiments, the recombinant protein expressed by the engineered microbe comprises one or more protease inhibitory domains of the LEKTI protein. Some non-limiting examples include one or more of domains D1, D2, D3, D4, D5, D6, D7, D8, D9, D10, D11, D12, D13, D14, and D15. According to some embodiments, the recombinant protein expressed by the engineered microbe comprises LEKTI inhibitory domain 6 or domains D8 to D11.

According to some embodiments, the LEKTI protein domains are effective to ameliorate the symptoms of Netherton Syndrome. As used herein, the terms "ameliorate", "ameliorating" and grammatical variations thereof mean to decrease the severity of the symptoms of a disease in a subject. In some embodiments, the LEKTI protein domains act as a competitive or non-competitive inhibitor of one or more proteases present on or in the skin of a mammal. In some embodiments, the LEKTI protein domain acts as a serine protease inhibitor. As used herein, the terms "protease" and "proteinase" are used interchangeably, with both terms referring to an enzyme that performs proteolysis.

According to some embodiments, the microbe is genetically modified by transfection/transformation with a recombinant DNA plasmid encoding the LEKTI protein domains. Other conventional or to-be-discovered methods for introducing DNA into a microbe may also be used in the present invention. According to some embodiments, the recombinant DNA plasmid comprises sequences encoding the LEKTI protein domain and one or more secretory peptides and/or cell penetration peptides. According to some embodiments, the LEKTI domains are operably linked to one or more recombinant protein domains that are effective to enhance secretion from the microbe and/or penetration of the mammal's skin.

The term "operably linked" refers to the association of nucleic acid sequences on a single nucleic acid fragment so that the function of one is regulated by the other or is not hindered by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, two proteins can be operably linked, such that the function of either protein is not compromised. Generally, operably linked means that the nucleic acid sequences being linked are contiguous and, where necessary to join two protein coding regions, contiguous and in the same reading frame.

As used herein the term "secretory peptides" or "secretory sequences" or "secretion tags" or "signal peptides" or "export signals" and grammatical variations thereof means any peptide sequence that is capable of targeting the synthesized protein to the secretory pathway of a cell. In some embodiments, the secretory peptide may be positioned on the N-terminal end of a recombinant protein, and may co-translationally or post-translationally target the tagged protein for secretion. According to some embodiments, at least one LEKTI domain is operably linked to a SecA domain (SEQ ID NO: 3).

Secretion peptides: According to some embodiments, the therapeutic LEKTI domain is operably linked to one or more secretion signals or export signals that tag the protein for transport through the secretory pathway. Any secretion signal that facilitates exit of the LEKTI protein out of the bacterial cell may be used as a secretion peptide. Non-limiting examples of secretion peptides signals are set forth in Table 3, below:

TABLE 3

| Amino Acid Sequence | SEQ ID NO: |
|---|---|
| MKKLAFAITAASGAAAVLSHHDAEA | 9 |
| WLDNRAFSKKFVPVVMATSVALFFLNLAFA | 10 |
| MAKKFNYKLPSMVALTLFGTAFTAHQANA | 11 |
| MKKRFLSICTMTIAALATTTMVNTSYA | 12 |
| NLKKQSKLILIFICIFTFFIMIIQSQFLMG | 13 |
| MKIFKLTSLTLAALTLAFPFSHVAQA | 14 |
| MKKTVIASTLAVSLGIAGYGLSGHEAH | 15 |
| MKKNKFLVYLLSTALITPTFATQTAFA | 16 |
| MKTRQNKYSIRKFSVGASSILIAALLFM GGGSAQA | 17 |
| MKNNNETRRFSIRKYTVGVVSIITGITI FVSGQHAQA | 18 |
| MKKKLSYMITIMLAFTLSLALGLFFNSAHA | 19 |
| MKKRFLSICTMTIAALATTTMVNTSYA | 77 |
| MKKKQVMLALTAAAGLGLTALHSAPAAKA | 78 (yfhK) |

According to some embodiments, the therapeutic LEKTI domain is operably linked to one or more signal sequences derived from endogenous proteins of *Staphylococcus epidermidis*. Non-limiting examples of secretion signal peptides derived from endogenous proteins of *Staphylococcus epidermidis* are set forth in Table 4 below:

TABLE 4

| Protein Name | Amino Acid Length | Signal Sequence | SEQ ID NO |
|---|---|---|---|
| *Staphylococcus epidermidis* | | | |
| Serine-aspartate repeat-containing protein F | 45 | MKKRRQGPINKRVDFLSNK VNKYSIRKFTVGTASILVGA TLMFGA | 20 |
| Glutamyl endopeptidase | 27 | MKKRFLSICTMTIAALATTT MVNTSYA | 21 |
| Bifunctional autolysin | 29 | MAKKFNYKLPSMVALTLFG TAFTAHQANA | 22 |
| Serine-aspartate repeat-containing protein G | 50 | MIKKNNLLTKKKPIANKSNK YAIRKFTVGTASIVIGAALLF GLGHNEAKA | 23 |
| Biofilm PIA synthesis deacetylase icaB | 30 | MKPFKLIFISALMILIMTNAT PISHLNAQA | 24 |
| Lipase | 35 | MKTRQNKYSIRKFSVGASSI LIAALLFMGGGSAQA | 25 |
| Epidermin leader peptide-processing serine protease epiP | 23 | MNKFKFFIVFLILSLVFLQNE YA | 26 |
| Fibrinogen-binding protein | 51 | MINKKNNLLTKKKPIANKSN KYAIRKFTVGTASIVIGATLL FGLGHNEAK A | 27 |
| Staphylococcal secretory antigen ssaA | 26 | MKKIATATIATAGIATFAFA HHDAQA | 28 |
| Extracellular elastase | 28 | MKNFSKFALTSIAALTVASP LVNTEVDA | 29 |
| n/a | 37 | MKNNNETRRFSIRKYTVGV VSIITGITIFVSGQHAQA | 30 |
| Uncharacterized lipoprotein SE_0145 | 19 | MRYLKRITIYISLLILVSG | 31 |
| Foldase protein prsA | 20 | MKLMNKIIVPVTASALLLGA | 32 |
| Probable cell wall amidase lytH | 40 | MKKIDSWLTKHGLKNRLTL VVIVIFIIFLILLFMFVNLSD | 33 |
| Membrane protein oxaA 2 | 19 | MKKKALLPLFLGIMIFLAG | 34 |
| Probable transglycosylase isaA | 28 | MKKTVIASTLAVSLGIAGYG LSGHEAHA | 35 |
| Probable quinol oxidase subunit 2 | 19 | MSKFKSLLLLFGTLILLSG | 36 |
| Probable transglycosylase sceD | 27 | MKKTLVASSLAIGLGVVAG NAGHDAHA | 37 |
| Bifunctional autolysin | 29 | MAKKFNYKLPSMVALTLFG TAFTAHQANA | 38 |
| Extracellular cysteine protease | 30 | MKKKLSYMITIMLAFTLSLA LGLFFNSAHA | 39 |
| Membrane protein oxaA 1 | 18 | MHKRLFITLLGFIILLAG | 40 |
| Uncharacterized lipoprotein SE_0144 | 19 | MRYLKRITIYISLLILVSG | 41 |
| N-acetylmuramoyl-L-alanine amidase sle1 | 25 | MQKKYITAIIGTTALSALAST HAQA | 42 |

TABLE 4-continued

| Protein Name | Amino Acid Length | Signal Sequence | SEQ ID NO |
|---|---|---|---|
| *Staphylococcus epidermidis* | | | |
| Uncharacterized lipoprotein SE_0142 | 22 | MKHSSKIIVFVSFLILTIFIGG | 43 |
| Phosphate-binding protein pstS | 20 | MKKWQLVGTTVLGASVLLG A | 44 |
| Accumulation-associated protein | 52 | MGKRRQGPINKKVDFLPNK LNKYSIRKFTVGTASILLGST LIFGSSSHEAKA | 45 |
| Staphylococcal secretory antigen ssaA | 26 | MKKIATATIATAGIATFAFA HHDAQA | 46 |
| Serine-aspartate repeat-containing protein F | 45 | MKKRRQGPINKRVDFLSNK VNKYSIRKFTVGTASILVGA TLMFGA | 47 |
| Glutamyl endopeptidase | 27 | MKKRFLSICTMTIAALATTT MVNTSYA | 48 |
| Lipase | 35 | MKTRQNKYSIRKESVGASSI LIAALLFMGGGSAQA | 49 |
| Extracellular elastase | 28 | MKNFSKFALTSIAALTVASP LVNTEVDA | 50 |
| Uncharacterized lipoprotein SE_1947 | 17 | MKKVLASATILSLMLVG | 51 |
| Uncharacterized lipoprotein SE_0186/SE_0187 | 22 | MKYYGKCISYISILILTFFIGG | 52 |
| Uncharacterized lipoprotein SERP2423 | 22 | MKHSSKIIVFVSFLILTIFIGG | 53 |
| Biofilm PIA synthesis deacetylase icaB | 30 | MKPFKLIFISALMILIMTNAT PISHLNAQA | 54 |
| Probable quinol oxidase subunit 2 | 19 | MSKFKSLLLLFGTLILLSG | 55 |
| Probable transglycosylase sceD | 27 | MKKTLVASSLAIGLGVVAG NAGHDAHA | 56 |
| Uncharacterized lipoprotein SERP2447 | 19 | MHYLKKVTIYISLLILVSG | 57 |
| N-acetylmuramoyl-L-alanine amidase sle1 | 25 | MQKKYITAIIGTTALSALAST HAQA | 58 |
| Uncharacterized lipoprotein SERP2445 | 22 | MKHSKKLLLCISFLLITFFIGG | 59 |
| Staphylococcal secretory antigen ssaA | 26 | MKKIATATIATAGIATFAFA HHDAQA | 60 |
| Uncharacterized lipoprotein SERP2443 | 19 | MRYLKKVTIYISLLILVSG | 61 |
| Glutamyl endopeptidase | 27 | MKKRFLSICTMTIAALATTT MVNTSYA | 62 |
| Phosphate-binding protein pstS | 20 | MKKWQLVGTTVLGASVLLG A | 63 |
| Bifunctional autolysin | 29 | MAKKFNYKLPSMVALTLFG TAFTAHQANA | 64 |

TABLE 4-continued

| Protein Name | Amino Acid Length | Signal Sequence | SEQ ID NO |
|---|---|---|---|
| *Staphylococcus epidermidis* | | | |
| Extracellular cysteine protease | 30 | MKKKLSYMITIMLAFTLSLA LGLFFNSAHA | 65 |
| Membrane protein oxaA 1 | 18 | MHKRLFITLLGFIILLAG | 66 |
| Uncharacterized lipoprotein SERP2422 | 22 | MRYLKKVTIYISLLILTIFIGG | 67 |
| Uncharacterized lipoprotein SERP1959 | 17 | MKKVLASATILSLMLVG | 68 |
| Uncharacterized lipoprotein SERP2453 | 22 | MKHSKKLLLCISFLLITVFISG | 69 |
| Uncharacterized lipoprotein SERP2465 | 22 | MKHSKKLLLCISFLLITFFISG | 70 |
| Probable transglycosylase isaA | 28 | MKKTVIASTLAVSLGIAGYG LSGHEAHA | 71 |
| Uncharacterized lipoprotein SERP2451 | 22 | MKHSKKLLLCISFLLITIFISG | 72 |
| Probable cell wall amidase lytH | 40 | MKKIDSWLTKHGLKNRLTL VVIVIFIIFLILLFMFVNLSD | 73 |
| Membrane protein oxaA 2 | 19 | MKKKALLPLFLGIMIFLAG | 74 |
| Foldase protein prsA | 20 | MKLMNKIIVPVTASALLLGA | 75 |
| Lipase | 35 | MKTRQNKYSIRKFSVGASSI LIAALLFMGGGSAQA | 76 |

According to some embodiments, the therapeutic LEKTI domain is operably linked to one or more secretion signal sequences derived from endogenous proteins of other bacteria. Non-limiting examples of secretion signal peptides derived from endogenous proteins of various bacteria are set forth in Appendix A.

According to some embodiments, the recombinant LEKTI domain is operably linked to a cell penetration peptide sequence that enhances the ability of the LEKTI domain to pass through a cell membrane. The term "enhance" as used to describe the cell penetration peptide/LEKTI, means that the cell penetration sequence improves the passage of recombinant LEKTI domain through a cell membrane relative to a recombinant LEKTI domain lacking the cell penetration sequence.

Cell penetration peptides: According to some embodiments, one or more cell penetrating peptides are used to mediate delivery of therapeutic proteins in vivo without using cell surface receptors and without causing significant membrane damage. According to some embodiments, one or more cell penetrating peptides are operably linked to therapeutic proteins to facilitate entry into skin cells (e.g. keratinocytes). Non-limiting examples are set forth in Table 5, below:

TABLE 5

| Cell penetrating sequence | SEQ ID NO |
|---|---|
| GRKKRRQRRRPPQ | 125 |
| GWTLNS AGYLLGKINLKALAALAKKIL | 126 |
| KLALKLALKALKAALKLA | 79 |
| WEAKLAKALAKALAKHLAKALAKALKACEA | 80 |
| KETWWETWWTEWSQPKKKRKV | 81 |
| RRRRRRRRR | 82 |
| LGTYTQDFNKFHTFPQTAIGVGAP | 83 |
| RQIKWFQNRRMKWKK | 84 |
| YGRKKRRQRRR | 85 |
| RGGRLSYSRRRFSTSTGR | 86 |
| RRLSYSRRRF | 87 |
| PIRRRKKLRRLK | 88 |

TABLE 5-continued

| Cell penetrating sequence | SEQ ID NO |
|---|---|
| RRQRRTSKLMKR | 89 |
| RRRRNRTRRNRRRVR | 90 |
| KMTRAQRRAAARRNRWTAR | 91 |
| TRRQRTRRARRNR | 92 |
| GRKKRRQRRRPPQ | 93 |
| GRRRRRRRRRPPQ | 94 |
| GWTLNSAGYLLGKINLKALAALAKKIL | 95 |
| KLALKLALKLALALKLA | 96 |
| MGLGLHLLVLAAALQGAWSQPKKKRKV | 97 |
| GALFLGWLGAAGSTMGAWSQPKKKRKV | 98 |
| GALFLGFLGAAGSTMGAWSQPKKKRKV | 99 |
| GALFLGFLGAAGSTMGAWSQPKSKRKV | 100 |
| KETWWETWWTEWSQPKKKRKV | 101 |
| KETWFETWFTEWSQPKKKRKV | 102 |

According to some embodiments, cell penetrating peptides comprise periodic amino acid sequences. Non-limiting examples of periodic cell penetrating sequences include: Polyarginines, R×n (wherein 4<n<17); Polylysines, K×n (wherein 4<n<17); arginine repeats interspaced with 6-aminocaprotic acid residues (RAca), wherein there are 2 to 6 arginine repeats; arginine repeats interspaced with 4-aminobutyric acid (RAbu), wherein there are 2 to 6 arginine repeats; arginine repeats interspaced with methionine, wherein there are 2 to 6 arginine repeats; arginine repeats interspaced with threonine, wherein there are 2 to 6 arginine repeats; arginine repeats interspaced with serine, wherein there are 2 to 6 arginine repeats; and arginine repeats interspaced with alanine, wherein there are 2 to 6 arginine repeats.

According to some embodiments, expression of the LEKTI domain is controlled by an operon and the amount of LEKTI provided to the mammal's skin is proportional to the availability of an extrinsic factor. For example, in some embodiments the recombinant LEKTI gene may be under the control of a xylose inducible promoter (e.g. xylose repressor (xylR), xylose operator (xylO), xylose isomerase gene (xylA) including the cis-acting catabolite-responsive element (CRE)), and the amount of recombinant LEKTI protein made available to the skin of the mammal controlled by the amount of exogenous xylose available to the recombinant microbe. According to some embodiments, the expression of the LEKTI domain is controlled by a promoter that is constitutively active. According to some embodiments, the expression of the LEKTI domain is controlled by a CmR promoter according to SEQ ID NO: 8.

According to some embodiments, the microbe is genetically modified by chromosomal integration of a DNA plasmid encoding the LEKTI protein domains. According to some embodiments, the DNA plasmid integrated into the bacterial chromosome comprises one or more sequences of the pJB38 vector. In some embodiments, the recombinant LEKTI protein is operably linked to an inducible promoter, ribosome binding site, export signal, and/or cell penetrating peptide in the pJB38 vector. In some embodiments, the recombinant LEKTI protein is fused in frame to a secretion peptide, and a synthetic propeptide. In some embodiments, the secretion peptide is yfhK secretion peptide from *Bacillus subtilis*. In some embodiments, the secretion peptide has at least 80%, 85%, 90%, 95%, 96%, 97%, 98%, or 99% identity to SEQ ID NO: 78. In some embodiments, the secretion peptide comprises, or consists of SEQ ID NO: 78.

According to some embodiments, the DNA plasmid encoding the recombinant LEKTI protein fused in frame to a secretion peptide and propeptide is integrated into the bacteria's chromosome. In some embodiments, the DNA plasmid encoding the recombinant LEKTI protein fused in frame to a secretion peptide and propeptide in integrated into the hld gene (delta-toxin gene). In some embodiments, the integrated nucleotide sequence encoding LEKTI protein fused in frame to a secretion peptide and propeptide is operably linked to one or more promoters. In some embodiments, the one or more promoters are endogenous, e.g., originate from the bacteria's chromosome. In some embodiments, the one or more promoters are $P_{yxiE}$ and P3. The $P_{yxiE}$ promoter is located immediately upstream of the hld gene and the P3 promoter is part of the neighboring accessory gene regulator (agr) operon. According to some such embodiments, the microbe is selected from the group consisting of *Bifidobacterium, Brevibacterium, Propionibacterium, Lactococcus, Streptococcus, Staphylococcus* (e.g., *S. epidermidis* and/or *S. hominis*), *Lactobacillus* (e.g., *L. acidophilus*), *Enterococcus, Pediococcus, Leuconostoc*, or *Oenococcus*, and mixtures thereof.

According to one aspect, the present disclosure provides a method of treating or ameliorating the effects of a skin disease of a mammal in need thereof comprising, providing onto a surface of the skin of the mammal a microbe genetically modified to express one or more LEKTI protein domains, wherein the LEKTI protein domains are effective to penetrate one or more layers of the mammal's skin and effective to inhibit activity of at least one serine protease in or on the mammal's skin. According to some embodiments, the microbe is adapted to live for a controlled duration on the surface of the mammal's skin and to provide a continuous supply of LEKTI protein domains.

According to another aspect, the present disclosure provides a kit for the treatment or amelioration of the effects of a skin disease of a mammal in need thereof comprising: (1) a composition comprising a microbe that is genetically modified to express one or more LEKTI protein domains, wherein the LEKTI protein domains are effective to penetrate one or more layers of the mammal's skin and effective to inhibit serine protease activity of at least one serine protease in or on the mammal's skin; and (2) reagents for applying the composition to the skin of the mammal. According to some embodiments, the microbes are adapted to live for a controlled duration on the surface of the mammal's skin and to provide a continuous supply of LEKTI protein domains.

In addition to the above components, the subject kits will further include instructions for use of the components and/or practicing the subject methods. These instructions may be present in the subject kits in a variety of forms, one or more of which may be present in the kit. One form in which these instructions may be present is as printed information on a suitable medium or substrate, such as a piece or pieces of paper on which the information is printed, in the packaging of the kit, or in a package insert. Yet another means would be a computer readable medium, such as diskette, or CD, on which the information has been recorded. Further, another means by which the instructions may be present is a website address used via the internet to access the information at a removed site. Any convenient means may be present in the kits.

The components of the kits may be packaged either in aqueous media or in lyophilized form. The kits will generally be packaged to include at least one vial, test tube, flask, bottle, syringe or other container means, into which the described reagents may be placed, and preferably, suitably aliquoted. Where additional components are provided, the kit will also generally contain a second, third or other additional container into which such component may be placed.

The kits of the present disclosure will also typically include a means for containing the reagent containers in close confinement for commercial sale. Such containers may include injection or blow-molded plastic containers into which the desired vials are retained.

Formulations

According to some embodiments the formulation for use according to the present invention can comprise any pharmaceutically effective amount of the recombinant bacteria to produce a therapeutically effective amount of the desired polypeptide or therapeutically effective domain(s) thereof, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about. 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% or more by weight of recombinant bacteria, the upper limit of which is about 90.0% by weight of recombinant, bacteria.

According to some embodiments, the formulation for use according to the present invention can comprise, for example, at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of recombinant bacteria.

According to some embodiments, the topical formulation can be in any form suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter. According to some embodiments, the formulation can include a living cell culture composition and can comprise at least one engineered bacterial strain that produces a therapeutically effective recombinant polypeptide or therapeutically effective domain(s) thereof. This engineered living cell culture composition can deliver the polypeptide directly to the skin for treating or preventing abnormal skin conditions.

Topical formulations include those in which any other active ingredient(s) is (are) dissolved or dispersed in a dermatological vehicle known in the art (e.g. aqueous or nonaqueous gels, ointments, water-in-oil or oil-in-water emulsions). Constituents of such vehicles can comprise water, aqueous buffer solutions, non-aqueous solvents (such as ethanol, isopropanol, benzyl alcohol, 2-(2-ethoxyethoxy) ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed can contain one or more components (for example, when the formulation is an aqueous gel, components in addition to water) selected from the following list: a solubilizing agent or solvent (e.g. a β-cyclodextrin, such as bydroxypropyl β-cyclodextrin, or an alcohol or polyol such as ethanol, propylene glycol or glycerol); a thickening agent (e.g. hydroxyethylceliulose, hydroxypropylcellulose, carboxymethylcellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (such as a mixture of dihydrogen phosphate and hydrogen phosphate salts, or a mixture of citric acid and a hydrogen phosphate salt).

A pharmaceutically acceptable carrier can also be incorporated in the formulation of the present invention and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers. The term "pharmaceutically acceptable" or "pharmaceutically acceptable carrier" is used herein to refer to a compound or composition that can be incorporated into a pharmaceutical formulation without causing undesirable biological effects or unwanted, interaction with other components of the formulation, "Carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue.

A film former, when it dries, forms a protective film over the site of application. The film inhibits removal of the active ingredient and keeps it in contact with the site being treated. An example of a film former that is suitable for use in this invention is Flexible Collodion, US P. As described in Remington: The Science and Practice of Pharmacy, 19th Ed. (Easton, PA: Mack Publishing Co., 1995), at page 1530, collodions are ethyl ether/ethanol solutions containing pyroxylin (a nitrocellulose) that evaporate to leave a film of pyroxylin. A film former can act additionally as a carrier. Solutions that dry to form a film are sometimes referred to as paints. Creams, as is well known in the arts of pharmaceutical formulation, are viscous liquids or semisolid emulsions, either oil-in-water or water-in-oil.

Cream bases are water-washable, and contain an oil phase, an emuisifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions are preferred formulations herein for treating large body areas, because of the ease of applying a more fluid composition. It is generally necessary that the insoluble matter in a lotion be finely-divided.

Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize or preserve the solute. Common examples of solvents used in preparing solutions are ethanol, water, propylene glycol or any other acceptable vehicles. As is of course well known, gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred "organic macromolecules," i.e., gelling agents, are cross-linked acrylic acid polymers such as the "carbomer" family of polymers, e.g., carboxypolyalkylenes that can be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxy-propyl cellulose, hydroxyethyl cellulose, hydroxypropyl methylcellulose, hydroxy-propyl methylcellulose phthaiate, and methylcellulose; gums such as tragacanth and xanthan gum; sodium alginate; and gelatin, In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, PA: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum.

Emulsifiable ointment bases, also known as absorbent ointment bases, contain little or no water and include, for example, hydroxystearin sulfate, anhydrous lanolin, and hydrophilic petrolatum.

Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight; see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxy-methylcellulose or the like as a base.

Enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter 6 of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol nionolaurace, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents.

Additional permeation enhancers will be known to those of ordinary skill in the art of topical drug delivery, and/or are described in the pertinent texts and literature. See, e.g., Percutaneous Penetration Enhancers, eds. Smith et al. (CRC Press, 1995)(incorporated herein by reference).

Various other additives can be included in the compositions of the present invention in addition to those identified above. These include, but are not limited to, antioxidants, astringents, perfumes, preservatives, emollients, pigments, dyes, humectants, propeliants, and sunscreen agents, as well as other classes of materials whose presence can be pharmaceutically or otherwise desirable. Typical examples of optional additives for inclusion in the formulations of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), β-tocopherol, γ-tocopherol, δ-tocopherol, ε-tocopherol, ζι-tocopherol, Z^-tocopherol, η-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), β-tocopherol, γ-tocopherol, 6-tocopherol, ε-tocopherol, ζι-tocopherol, $\zeta_2$-tocopherol, η-tocopherol, and retinol (Vitamin A), and/or pharmaceutically acceptable salts, esters, amides, or other derivatives thereof. A preferred tocopherol compound is a-tocopherol. Additional agents include those that are capable of improving oxygen supply in skin tissue, as described, for example, in Gross, et al, WO 94/00098 and Gross, et al, WO 94/00109, both assigned to Lancaster Group AG (incorporated herein by reference). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycmnamate, octyl salicylate, oxybenzone, padirnate O, phenylbenzirmdazole sulfonic acid, sulisobenzone, titanium dioxide, trolamine salicylate, zinc oxide, ensulizole, meradiraate, octinoxate, octisalate, and octocrylene. See Title 21. Chapter 1. Subchapter D. Part 352. “Sunscreen drug products for over-the-counter human use” incorporated herein in its entirety.

Other embodiments can include a variety of non-carcinogenic, non-irritating healing materials that facilitate treatment with the formulations of the invention. Such healing materials can include nutrients, minerals, vitamins, electrolytes, enzymes, herbs, plant extracts, glandular or animal extracts, or safe therapeutic agents that can be added to the formulation to facilitate the healing of dermal disorders.

The amounts of these various additives are those conventionally used in the cosmetics field, and range, for example, from about 0.01% to about 20% of the total weight of the topical formulation.

The formulations of the invention can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds.

Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. In other embodiments, other agents can also be added, such as repressors and inducers, i.e., to inhibit (i.e. glycose) or induce (i.e. xylose) the production of the polypeptide of interest. Such additives can be employed provided they are compatible with and do not interfere with the function of the formulations.

The formulations can also contain irritation-mitigating additives to minimize or eliminate the possibility of skin irritation or skin damage resulting from the chemical entity to be administered, or other components of the composition.

Suitable irritation-mitigating additives include, for example: a-tocopherol; monoamine oxidase inhibitors, particularly phenyl alcohols such as 2-phenyl-1-ethanol; glycerin; salicylates; ascorbates; ionophores such as monensin; amphophilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation.

Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites.

Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycmnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil.

A cream, lotion, gel, ointment, paste or the like can be spread on the affected surface and gently rubbed in. A solution can be applied in the same way, but more typically will be applied with a dropper, swab, or the like, and carefully applied to the affected areas.

The application regimen will depend on a number of factors that can readily be determined, such as the severity of the condition and its responsiveness to initial treatment, but will normally involve one or more applications per day on an ongoing basis. One of ordinary skill can readily determine the optimum amount of the formulation to be administered, administration methodologies and repetition rates. In general, it is contemplated that the formulations of the invention will be applied in the range of once or twice weekly up to once or twice daily.

The pharmaceutical compositions of the invention comprise one or more active ingredients, e.g. therapeutic agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxy-methylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl-cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

The following examples are provided to further illustrate the methods of the present invention. These examples are illustrative only and are not intended to limit the scope of the invention in any way.

EXAMPLES

Example 1

Method of Integration of the hLEKTI-d6 Cassette into the Chromosome of *S. epidermidis* SEΔΔΔ.

The chromosomal hLEKTI-d6 expressing strain was constructed by the procedure that follows. The expression cassette from plasmid pLEKTI-27a-d6 (FIGS. 1A and 1B) containing human hLEKTI-d6 domain fused in frame to the *Bacillus subtilis* yfhK secretion peptide (SP) and a synthetic propeptide (pro9; (5)) was exchanged by homologous recombination into the delta-toxin gene (hld, SE1634, based on Genbank accession AE015929.1 of *S. epidermidis* ATCC 12228). Transcription of the hLEKTI-d6 gene from the integrated cassette was designed to be driven by the $P_{yxiE}$ promoter (6) derived from pLEKTI-27a-d6 and a native promoter, P3, of the SE1634 gene located immediately upstream of the $P_{yxiE}$ promoter in the chromosome. Promoter P3 is a part of/regulated by quorum sensing of the neighboring accessory gene regulator (agr) operon (7). It is activated by agrA protein (FIGS. 1A and 1B) and recognized by RNAP III transcriptional complex. The coding sequence of SE1634 between the start and stop codons was exchanged with the $P_{yxiE}$-yfhK SP-pro9-LEKTI-d6 cassette, keeping intact the P3 promoter, ribosome binding site (RBS), and 3' untranslated end of the SE1634 mRNA.

For chromosomal integration, the exchange plasmid, pJB38-SE1634-KO-$P_{yxiE}$-d6-KI, was designed using Benchling (an online sequence design tool, www.benchling-.com). A set of eight overlapping oligonucleotide primers were designed to amplify four DNA fragments by PCR using a high-fidelity DNA polymerase (Table 6). Four PCR reactions using Q5® High-Fidelity 2× Master Mix (New England Biolabs (NEB)) were performed on the following DNA templates: 1) pJB38 plasmid ((8); one reaction producing ~7 kb), 2) *S. epidermidis* NRRL B-4268 strain genomic DNA (two reactions, each producing a ~1 kb fragment, one flanking the 5' and one flanking the 3' region of SE1634 gene), and 3) pLEKTI-27a-d6 (one reaction producing a fragment of 690 bp encoding the LEKTI-d6 expression cassette). All reactions were confirmed by agarose gel electrophoresis for the presence and correct sizes of amplified DNA fragments.

primers. Sequence-verified plasmids were transformed in an *E. coli* dcm− strain to obtain unmethylated plasmid DNA. Plasmid DNA from the dcm− strain was also sequence-verified and transformed by electroporation into *S. epidermidis* $SE_{\Delta\Delta\Delta}$ cells. Plasmid was also isolated and the sequence-verified from strain $SE_{\Delta\Delta\Delta}$.

Plasmid pJB38-SE1634-KO-$P_{yxiE}$-d6-KI was integrated into the chromosome of $SE_{\Delta\Delta\Delta}$ by growing cells at the non-permissive temperature for plasmid replication, 44° C. Four colonies of $SE_{\Delta\Delta\Delta}$ containing pJB38-SE1634-KO-$P_{yxiE}$-d6-KI were streaked on tryptic soy agar (TSA) containing 100 μg/mL D-alanine (to supplement auxotrophy) and 10 μg/mL chloramphenicol (to select for the plasmid) and incubated at 44° C. for 24-36 hours. Resulting colonies were analyzed by PCR with primers anchored in 5' and 3' flanking regions outside of integration and plasmid-specific primers. To obtain a second recombination event, confirmed integrant colonies were incubated in tryptic soy broth (TSB) with 100 μg/mL D-alanine, and no chloramphenicol, at the permissive temperature for plasmid replication, 30° C. After one or two passages in TSB+D-ala/no chloramphenicol, cells were plated on TSA+D-ala for single colonies. Colonies were assayed for plasmid loss by patching on TSA+/− chloramphenicol. Choramphenicol-sensitive (Cam-S) colonies were analyzed by PCR with primer pairs located outside and inside of allelic exchange region. Eight colonies were identified that were both Cam-S and PCR-positive.

TABLE 6

Primers to construct and analyze chromosomal integration of exchange plasmid pJB38-SE1634-KO-PyxiE-d6-KI

| Number | Name | bp | Sequence |
|---|---|---|---|
| 97 | GA-pJB-3'2-F | 31 | CGG ATC CTA CCC GGA TCG ATC CTC TAG A (SEQ ID NO: 127) |
| 166 | 5' of SEagr-pJB-GA-F | 58 | TTC GAG CTC GCC CGC TAA GCG CTA CCC GCG AGC TGA TAA AAA TCT TAA AGACAG CTC T (SEQ ID NO: 128) |
| 241 | 5' of SE1634-GA-R | 35 | TAA TTT TTG AAT GAG TCT ATT GTA ACT TTT GTA AC (SEQ ID NO: 129) |
| 242 | 5' of SE1634-GA-d6-F | 50 | CAA TAG ACT CAT TCA AAA ATT CAT TAA TTT CGA CTT TTG CCC TC (SEQ ID NO: 130) |
| 243 | PyxiE-GA-3'SE1634R | 46 | CGA AAG GAG TGA AGT TAT AAT GAC GAT TAC AGA ATC AAC TAT CTG C (SEQ ID NO: 131) |
| 244 | 3' of SE1634-F | 30 | CAT TAT AAC TTC ACT CCT TTC GAA TTA AGG (SEQ ID NO: 132) |
| 245 | 3' of SE1634-GA-R | 58 | CGA TCC GGG TAG GAT CCG CTA AGG GTT ATA TTT ACT CGT ATA GTT TAG TCA G (SEQ ID NO: 133) |
| 146 | 5' outSEagr-F | 25 | CAGAAATGTGGAATAACGGTTATGC (SEQ ID NO: 134) |
| 147 | 3' outSEagr | 22 | GCTTCGACTGAATCTGGTCAAG (SEQ ID NO: 135) |

One microliter of each PCR reaction was combined and assembled using NEBuilder® HiFi DNA Assembly Master Mix (NEB). A portion of the assembly reaction was transformed into competent *Escherichia coli* NEB 5-α cells. The plasmids from transformants were analyzed by agarose gel electrophoresis and by DNA sequencing using the PCR The chromosomal cassette in all eight strains was PCR-amplified and sequence-verified. All eight strains were also confirmed for D-ala auxotrophy by their inability to grow without D-ala supplementation in growth media. The chromosomal constructs were stored and designated as: SE350, SE351, SE352, SE353, SE354, SE355, SE356, and SE357.

Figure 1B:
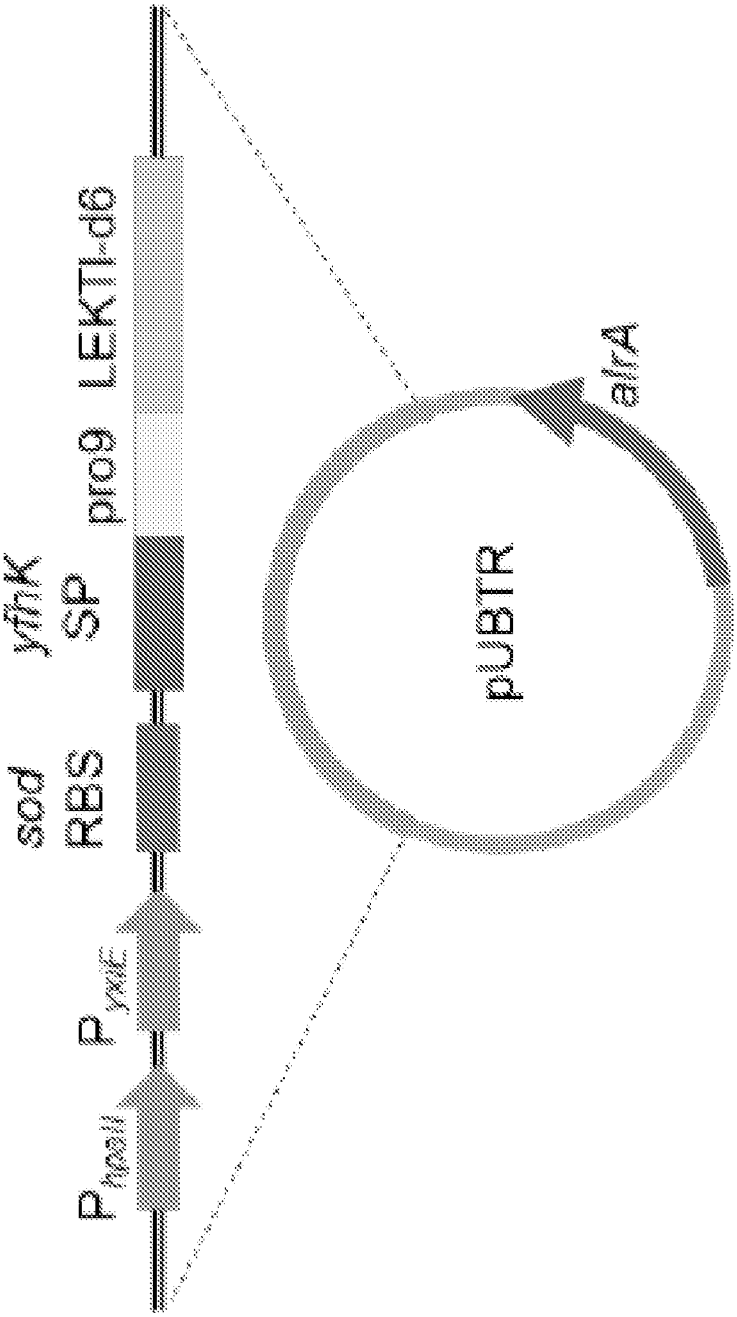

Each strain was confirmed to contain a single copy of the [-$P_{yxiE}$-RBSsod-SPyfhK-pro9-LEKTI-d6-] cassette inserted into the delta-toxin gene encoded by *S. epidermidis* gene SE1634, located downstream of the P3 promoter immediately outside of the agrACDB operon, encoding quorum sensing regulatory proteins (FIGS. 1A and 1B). The same cassette is located downstream of the pUBTR-114 hpaII promoter (9) in plasmid pLEKTI-27a-d6. Plasmid pUBTR-114 is a derivative of the *B. subtilis* plasmid, pUB110, which is known to be moderate to low copy number (~10-50; (10)). The exact copy number of pLEKTI-27a-d6 has not been experimentally determined.

In both chromosomal and plasmid constructs, hLEKTI-d6 is constitutively expressed and protein is secreted to the culture medium. However, several key features distinguish the chromosomal construct strain from the plasmid construct strain: 1) The chromosomal construct is single copy, whereas the plasmid construct is expected to be multicopy. This may impact the overall level of expression of the hLEKTI-d6 gene; 2) The chromosomal construct strain has a deletion of the delta-toxin gene due to insertion of the hLEKTI-d6 expression cassette; 3) The chromosomal construct strain retains the auxotrophy of $SE_{\Delta\Delta\Delta}$ (dependence on D-alanine supplementation) since, unlike in strain 27a, the auxotrophy is not complemented by the plasmidic alrA gene; and 4) The chromosomal construct may have an enhanced intrinsic stability of the expression cassette due to its integration into the chromosome versus being carried on an extrachromosomal genetic element (plasmid).

Example 2

The Chromosomal Construct Strains Require D-Alanine Supplementation and Constitutively Express Secreted hLEKTI-d6 at Higher Levels than Plasmid Construct Strain 27a.

The growth of the independently isolated 8 sequence-verified strains with the chromosomal hLEKTI-d6 expression cassette (SE350-SE357) was examined in TSB with and without D-alanine supplementation (100 μg/mL). Cultures were grown for 22 hours at 30° C. with aeration. In the absence of D-alanine, no growth was observed for the chromosomal construct strains, however, saturated growth was observed in the presence of D-alanine (Table 7). As expected, the plasmid-containing strain, 27a, was able to grow in the absence of D-alanine due to complementation of auxotrophy by the alanine racemase gene present on plasmid pLEKTI-27a-d6.

TABLE 7

Growth of chromosomal construct strains with and without D-alanine supplementation.

| | OD600 of overnight culture | |
|---|---|---|
| Strain | +D-ala | −D-ala |
| 27a | ND | 12.9 |
| SE350 | 8.2 | 0 |
| SE351 | 8.5 | 0 |
| SE352 | 8.7 | 0 |
| SE353 | 8.0 | 0 |
| SE354 | 9.8 | 0 |
| SE355 | 8.8 | 0 |
| SE356 | 9.6 | 0 |
| SE357 | 8.8 | 0 |

Growth in TSB;
ND: not done;
D-ala: 100 μg/mL

Figure 2:
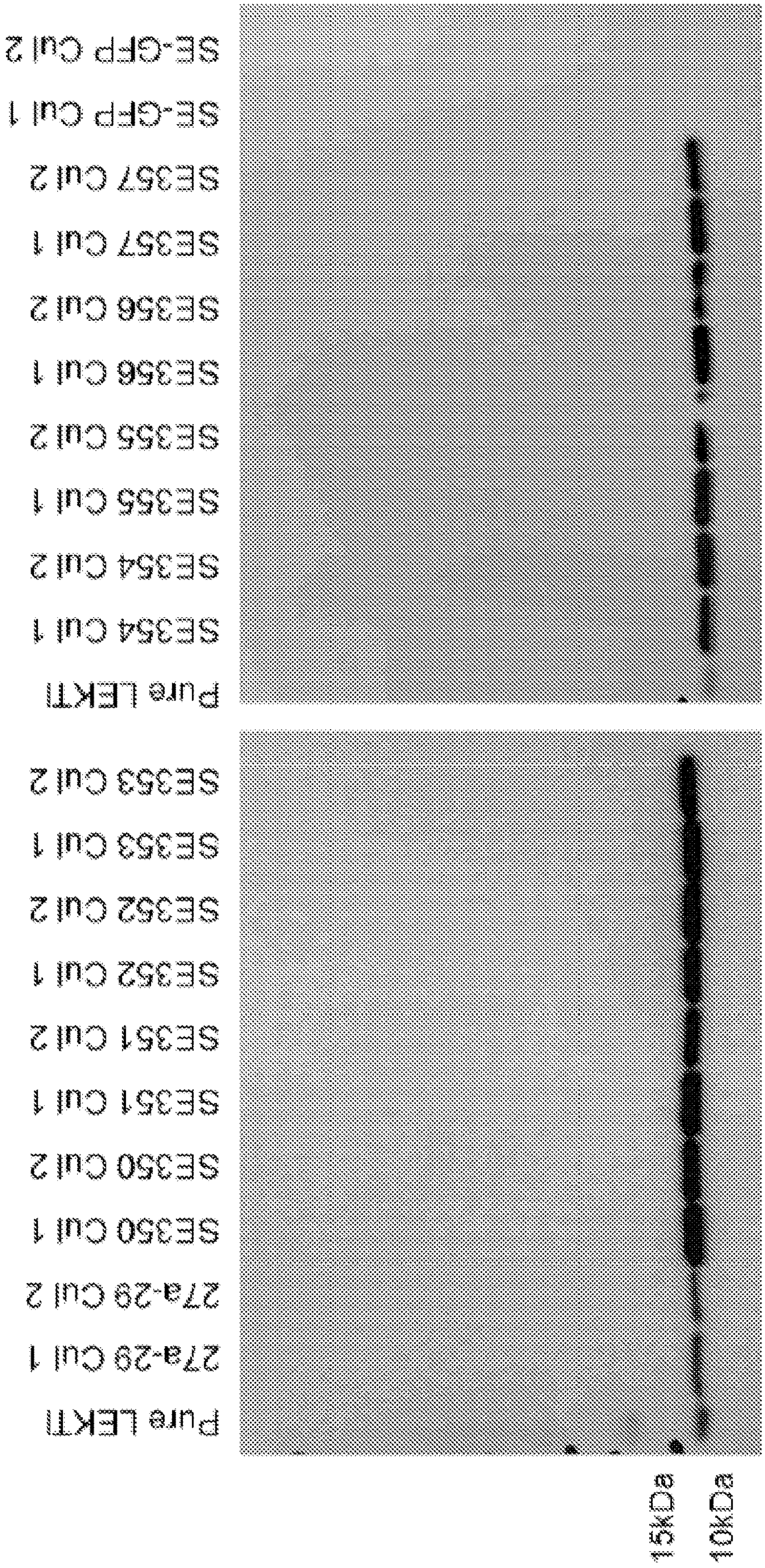
FIG. 2 depicts a Western blot characterization of expression of hLEKTI-d6 from the culture supernatants of *S. epidermidis* chromosomal hLEKTI-d6 strains.

Duplicate cultures of the chromosomal construct strains SE350-SE357, and the plasmid construct strain 27a, were grown in TSB+D-alanine (100 μg/mL) for 22 hours at 30° C. with aeration, and culture supernatants were analyzed by western blot. Culture supernatants were sampled and run on a 12% SDS-PAGE gel. The electrophoresed proteins were transferred to a PVDF membrane by western blot, and hLEKTI-d6 was detected by the primary chicken IgY antibody (anti-LEKTI-d6 antibody #337) and a secondary goat anti-chicken IgY horseradish peroxidase (HRP) conjugate. The HRP reaction was detected by chemiluminescence. Results showed that the western blot bands for the chromosomal construct strains were generally heavier than the those for the plasmid construct strain 27a (FIG. 2). As expected, no band was detected in the negative control strain, expressing green fluorescent protein in pUBTR-114 (SE-GFP).

Figure 3A:
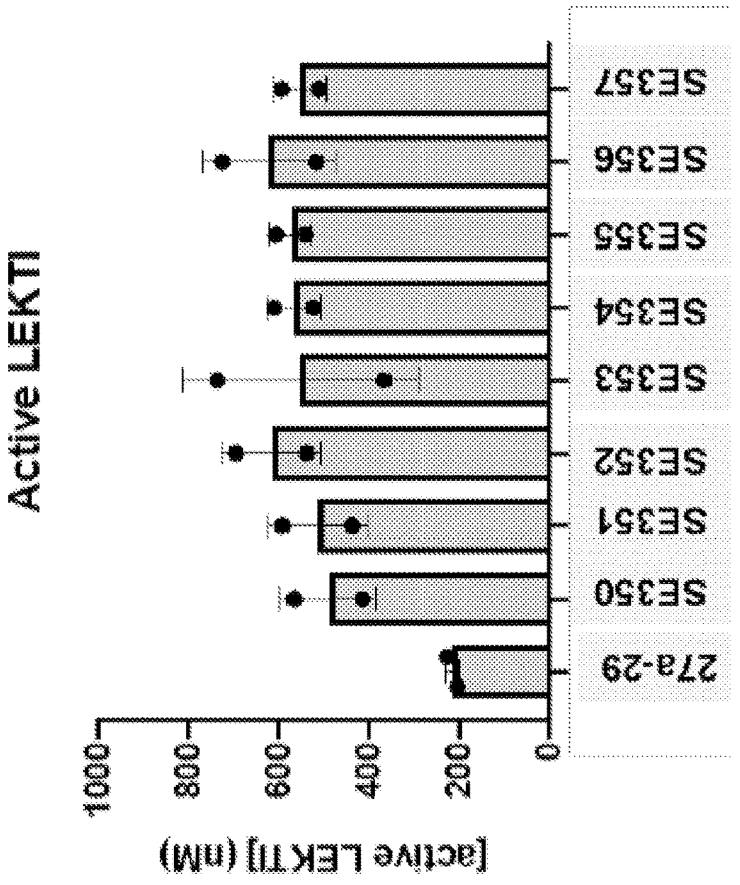
FIG. 3A depicts a bar graph measuring active LEKTI expressed from an episomal plasmid compared to chromosomal expression. Values are presented as mean of the technical duplicates (% CV≤10%).
Figure 3B:
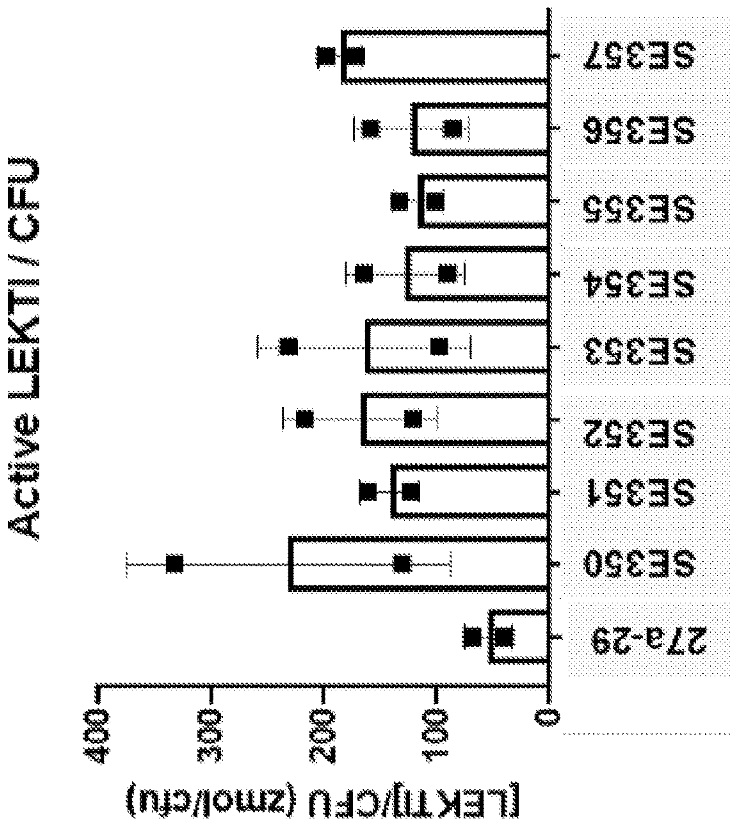
FIG. 3B depicts a bar graph measuring active LEKTI per CFU expressed from an episomal plasmid compared to chromosomal expression. Values are presented as mean of the technical duplicates (% CV≤10%).
Figure 4B:
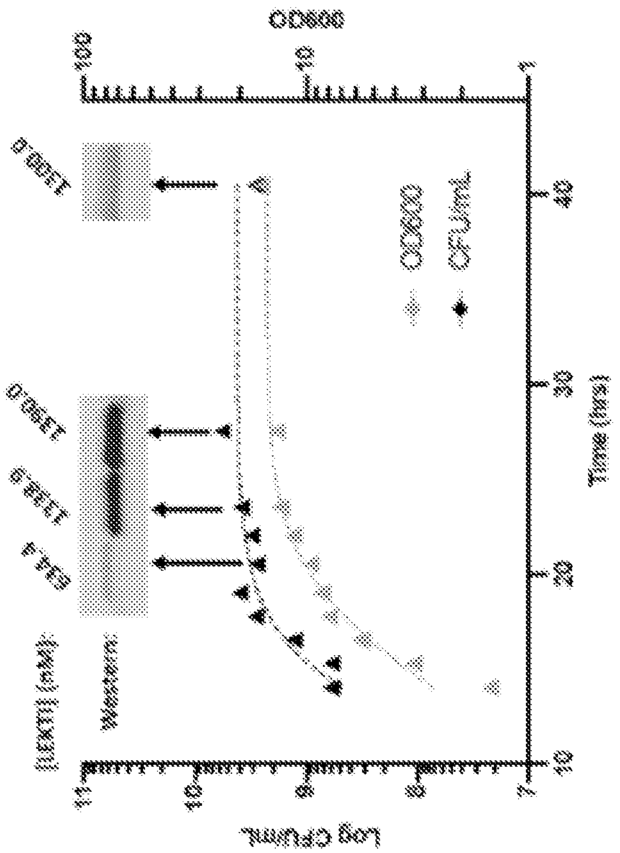
FIG. 4B depicts a graph comparing expression of LEKTI during logarithmic and stationary growth phases in strain SE352.
Figure 4A:
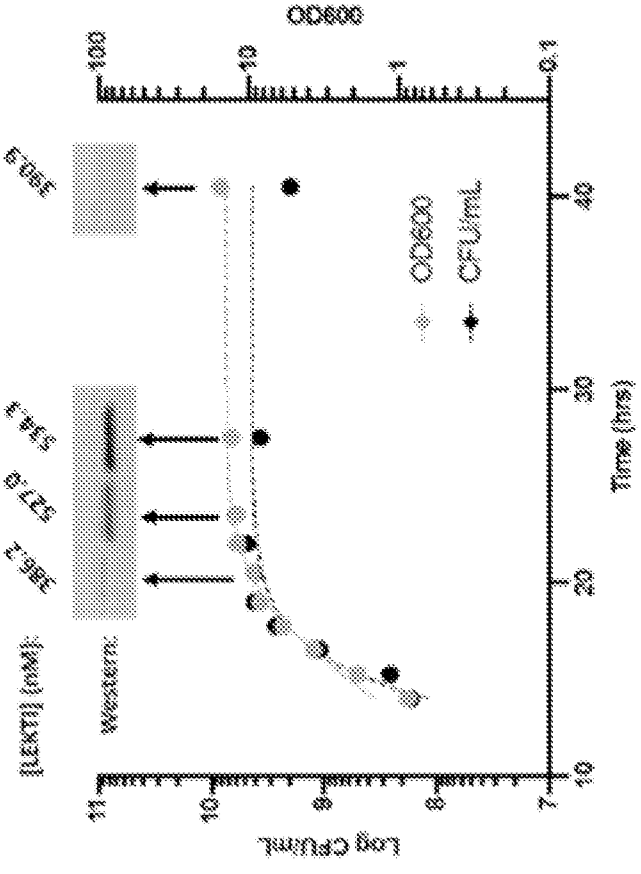
Figure 4C:
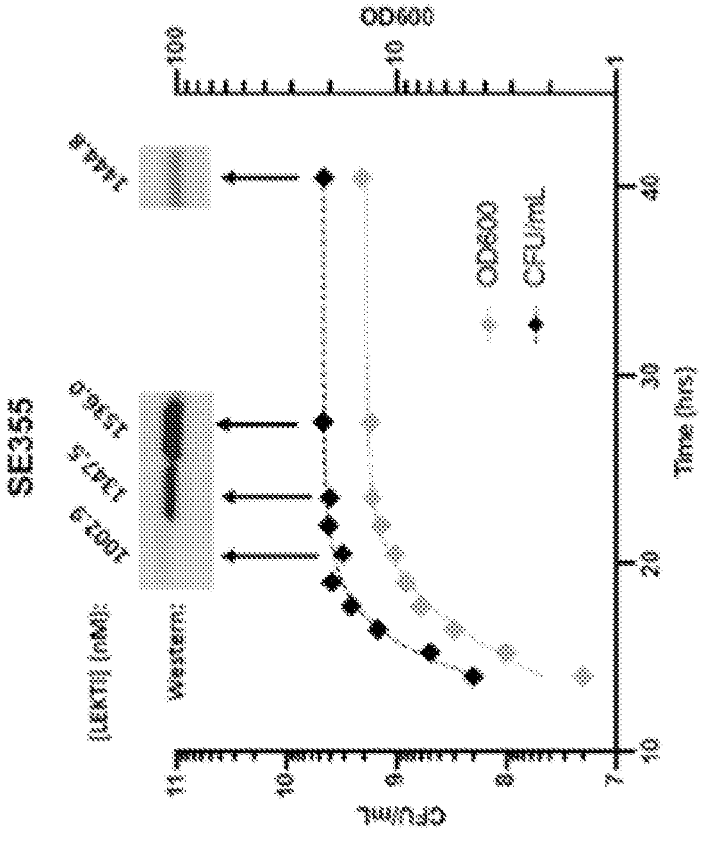
FIG. 4C depicts a graph comparing expression of LEKTI during logarithmic and stationary growth phases in strain SE355.

The levels of active hLEKTI-d6 related species in the *S. epidermidis* culture supernatants analyzed by western blot in FIG. 2 were quantified. Briefly, the broths were diluted 1:10 in Assay Buffer (50 mM Tris, 150 mM NaCl, 0.05% (w/v) Brij-35, pH 8.0) containing 3 nM activated hKLK14, and those were serially diluted in 2-fold steps in assay buffer containing 3 nM activated hKLK14 to reach a final volume of 25 μL of the mixes per well. The reaction was started by the addition of 25 μL of assay buffer containing 30 μM Boc-VPR-AdMC and monitored for 10 min in 1 min intervals at 23° C. in a Biotek Hybrid plate reader (Ex/Em=380/460 nm). In each well, the final concentrations of each component were as follows: 1.5 nM activated hKLK14, 15 μM Boc-VPR-AdMC and 10 to 0.32% (v/v) of spent media sources. The media control samples SE-GFP and TSB+D-ala displayed no substantial hKLK14 inhibition at concentrations up to 5%. Since the samples had to be split in three 96-well plates, each plate contained its own calibration curve using purified His-tagged hLEKTI-d6 (lot DM29/24) in the range of 0-4 nM protein. This procedure was performed to avoid a plate-to-plate bias in the calculated concentrations of hLEKTI-d6 species in the broths. Each sample and its respective dilutions were measured in technical duplicates. The rates of hKLK14 reaction were calculated using the data points from 0-4 min of reaction and summarized results are shown in FIG. 3.

All samples contained measurable levels of active hLEKTI-d6 species, which ranged from 39-333 zmol/CFU. There was a high variation in the zmol/CFU hLEKTI-d6 levels between the biological replicates of the same strain. The strains expressing chromosomal hLEKTI-d6 displayed 2- to 5-fold higher levels of active hLEKTI-d6 species compared to the strain expressing LEKTI-d6 in an episomal plasmid. This result was consistent with the observation by western blot that the chromosomal construct strains expressed more hLEKTI-d6 protein, as detected with anti-LEKTI-d6 antibody #337.

The timing of hLEKTI-d6 expression was examined in growth curve experiments with plasmid construct strain 27a, and two chromosomal hLEKTI-d6 strains, SE352 and SE355. Cultures were grown in TSB at 30° C. with aeration and culture supernatants were sampled at the onset of stationary phase and at several time points during stationary phase. Results showed that while the optical density at 600 nm did not change between the 19 and 23.5 hr time points, hLEKTI-d6 production in plasmid and chromosomal construct strains was enhanced at the later time point, as visualized by western blot and quantified by KLK14 assay. Enhancement of hLEKTI-d6 production during stationary phase may in part be due to stimulation by nutrient depletion (phosphate depletion) of the $P_{yxiE}$ promoter driving expression of the hLEKTI-d6 gene in both plasmid and chromosomal construct strains (FIGS. 1A and 1B). The overall higher levels of hLEKTI-d6 protein observed in the chromosomal construct strain cultures suggest additional factors are involved in hLEKTI-d6 protein production in these strains.

TABLE 8

Exemplary Sequences

| Description | Sequence |
|---|---|
| PyxiE (SEQ ID NO: 120) | ACGATTACAGAATCAACTAT CTGCGTGATCATTTAATTGA AGCGCGCGAAGCCATTGCGG ACGGCGTTGAATTAATCGGA TACACATCATGGGGGCCAAT TGACCTTGTCAGCGCATCTA CTGCGGAAATGAAAAAGCGC TACGGCTTCATTTATGTAGA CCGGGACAATGAAGGAAATG GAACATTTAACCGCATCAAG AAAAAAAGCTTCAACTGGTA TCAGCAGGTTATCGCCACAA ACGGAGAGAGTCTCTGACAA TTTTTTGAAAACTCATGCGC TTCAATTGACAATAACGAAA TGCAGGCGGACAATAAAAGA GAAAGg |
| RBSsod (SEQ ID NO: 121) | GGTACCTTAGGAGGATGATT ATTT |
| yfhK (SEQ ID NO: 122) | ATGAAAAAGAAACAAGTAAT GCTCGCTTTAACAGCTGCCG CAGGACTGGGTTTGACAGCA CTTCATTCCGCTCCCGCAGC AAAAGCT |
| Pro9 (SEQ ID NO: 123) | TTAGAAATTTCATCAACATG TGATGCA |
| $P_{yxiE}$-RBSsod-SPyfhK-pro9-LEKTI-d6 (SEQ ID NO: 124) | acgattacagaatcaactat ctgcgtgatcatttaattga agcgcgcgaagccattgcgg acggcgttgaattaatcgga tacacatcatgggggccaat tgaccttgtcagcgcatcta ctgcggaaatgaaaaagcgc tacggcttcatttatgtaga ccgggacaatgaaggaaatg gaacatttaaccgcatcaag aaaaaaagcttcaactggta tcagcaggttatcgccacaa acggagagagtctctgacaa ttttttgaaaactcatgcgc ttcaattgacaataacgaaa tgcaggcggacaataaaaga gaaaggtcgactaccttagg aggatgattatttatgaaaa |

TABLE 8-continued

Exemplary Sequences

| Description | Sequence |
|---|---|
| | agaaacaagtaatgctcgct ttaacagctgccgcaggact gggtttgacagcacttcatt ccgctcccgcagcaaaagct gccgaattcttagaaatttc atcaacatgtgatgcagaat ctggtaaagcaacgagttac gctgaattgtgctcagaata ccgtaagttagtcagaaacg gaaagttggcgtgtactcgt gagaacgaccctatccaggg accggacggcaaggtacatg gaaatacttgcagtatgtgc gaggtgtttttccaggcgga ggaagaagaaaagaagaaaa aggagggcaaaagtcgaaat taatgaataa |

REFERENCES

1. Phanaksri T, Luxananil P, Panyim S, Tirasophon W. 2015. Synergism of regulatory elements in sigma(B)- and sigma(A)-dependent promoters enhances recombinant protein expression in *Bacillus subtilis*. J Biosci Bioeng 120:470-5
2. Ozturk S, Ergun B G, Calik P. 2017. Double promoter expression systems for recombinant protein production by industrial microorganisms. Appl Microbiol Biotechnol 101:7459-75
3. Kong K F, Vuong C, Otto M. 2006. *Staphylococcus quorum* sensing in biofilm formation and infection. Int J Med Microbiol 296:133-9
4. Tan L, Li S R, Jiang B, Hu X M, Li S. 2018. Therapeutic Targeting of the *Staphylococcus aureus* Accessory Gene Regulator (agr) System. Front Microbiol 9:55
5. Le Loir Y, Gruss A, Ehrlich S D, Langella P. 1998. A nine-residue synthetic propeptide enhances secretion efficiency of heterologous proteins in *Lactococcus lactis*. J Bacteriol 180:1895-903
6. Antelmann H, Scharf C, Hecker M. 2000. Phosphate starvation-inducible proteins of *Bacillus subtilis*: proteomics and transcriptional analysis. J Bacteriol 182: 4478-90
7. Otto M. 2004. Quorum-sensing control in Staphylococci—a target for antimicrobial drug therapy? FEMS Microbiol Lett 241:135-41
8. Bose J L, Fey P D, Bayles K W. 2013. Genetic tools to enhance the study of gene function and regulation in *Staphylococcus aureus*. Appl Environ Microbiol 79:2218-24
9. Zyprian E, Matzura H. 1986. Characterization of signals promoting gene expression on the *Staphylococcus aureus* plasmid pUB110 and development of a gram-positive expression vector system. DNA 5:219-25
10. Leonhardt H. 1990. Identification of a low-copy-number mutation within the pUB110 replicon and its effect on plasmid stability in *Bacillus subtilis*. Gene 94:121-4

INCORPORATION BY REFERENCE

The entire disclosure of each of the patent documents, including patent application documents, scientific articles, governmental reports, websites, and other references referred to herein is incorporated by reference herein in its entirety for all purposes. In case of a conflict in terminology, the present specification controls. All sequence listings, or Seq. ID. Numbers, disclosed herein are incorporated herein in their entirety.

The following references, to the extent that they provide exemplary procedural or other details supplementary to those set forth herein, are specifically incorporated herein by reference.

Although illustrative embodiments of the present invention have been described herein, it should be understood that the invention is not limited to those described, and that various other changes or modifications may be made by one skilled in the art without departing from the scope or spirit of the invention.

What is claimed is:

1. A recombinant microorganism capable of secreting one or more therapeutic polypeptides, wherein the recombinant microorganism is selected from the group consisting of *Moraxella, Corynebacteria, Pasteurella, Haemophilus, Streptococcus*, and *Staphylococcus*, and wherein the recombinant microorganism comprises (i) a first coding sequence comprising a nucleic acid sequence encoding the one or more therapeutic polypeptides, wherein the one or more therapeutic polypeptides comprise LEKTI domain 6 (D6);

(ii) a second coding sequence comprising a nucleic acid sequence encoding one or more secretion peptides that are not associated with the one or more therapeutic polypeptide in nature; and (iii) a third coding sequence comprising a nucleic acid sequence encoding a pro-peptide, wherein the nucleic acid sequence encoding the pro-peptide is set forth in SEQ ID NO: 123, wherein the first coding sequence, the second coding sequence, and the third coding sequence are linked to a promoter and wherein the first coding sequence, the second coding sequence, and the third coding sequence are chromosomally integrated into a hld gene.

2. The recombinant microorganism of claim 1, wherein the recombinant microorganism is attenuated by auxotrophy.

3. The recombinant microorganism of claim 2, wherein the recombinant microorganism is a D-alanine auxotroph.

4. The recombinant microorganism of claim 1, wherein the promoter is P3 and/or $P_{yxiE}$, wherein $P_{yxiE}$ comprises SEQ ID NO: 120.

5. The recombinant microorganism of claim 1, wherein the secretion peptide is *Bacillus subtilis* yfhK gene; and/or wherein the secretion peptide comprises SEQ ID NO: 122.

6. The recombinant microorganism of claim 1, wherein the microorganism is *Staphylococcus epidermidis.*

7. The recombinant microorganism of claim 1, wherein the recombinant microorganism secretes the one or more therapeutic polypeptide.

8. A live biotherapeutic composition comprising a recombinant microorganism, wherein the recombinant microorganism is selected from the group consisting of *Moraxella, Corynebacteria, Pasteurella, Haemophilus, Streptococcus*, or *Staphylococcus*, wherein the recombinant microorganism comprises:

a nucleic acid sequence comprising one or more nucleic acid sequences encoding (i) LEKTI protein domain 6 (D6), (ii) one or more secretion peptides, (iii) a pro-peptide comprising SEQ ID No: 123, and (iv) a promoter, wherein the nucleic acid sequence is integrated into the hld gene in the chromosome of the cell, and wherein the recombinant microorganism is capable of secreting the LEKTI protein domain 6 (D6).

9. The composition of claim 8, wherein the secretion peptide is from *Bacillus subtilis* yfhK gene; and/or wherein the secretion peptide comprises SEQ ID NO: 122.

10. The composition of claim 8, wherein the promoter is $P_{yxiE}$, wherein $P_{yxiE}$ comprises SEQ ID NO: 120.

11. The composition of claim 10, wherein the LEKTI protein domain 6, the one or more secretion peptides, and the pro-peptide are under the control of an endogenous promoter; and/or wherein the endogenous promoter is P3; and/or wherein the arrangement of the LEKTI protein domain 6, the one or more secretion peptides, and the pro-peptide are in-frame.

12. The composition of claim 8, wherein the recombinant microorganism is *Staphylococcus epidermidis.*

13. The composition of claim 8, comprising a pharmaceutically acceptable carrier, wherein the pharmaceutically acceptable carrier is selected from the group consisting of an aqueous solution, an emulsion, a cream, a lotion, a gel, and an ointment.

14. A kit comprising the composition of claim 8 and instructions for use.

15. A method of treating a disease or disorder comprising administering to a subject in need thereof the composition of claim 8, wherein the disease or disorder is selected from a skin disease, a disease or disorder associated with pain, cancer, and a viral infection, wherein the skin disease is selected from the group consisting of pruritus, rosacea, psoriasis, atopic dermatitis, Ichthyosis vulgaris, and Netherton Syndrome;

wherein the disease or disorder associated with pain is selected from the group consisting of acute pain, chronic pain, nociceptive pain, neuropathic pain, traumatic pain, inflammatory pain, post-operative incision pain, pain associated with cancer, fracture pain, osteoporotic pain, bone cancer pain, and gout joint pain;

wherein the cancer is selected from the group consisting of malignant melanoma, colon cancer, breast cancer, lung cancer, ovarian cancer, gastric cancer, oral tongue squamous cell carcinoma, squamous cell cancer, prostate cancer, pancreatic cancer, liver cancer, kidney cancer, bladder cancer, cervical cancer, endometrial cancer, gallbladder cancer, brain cancer and oral cancer; and wherein the viral infection is selected from a group consisting of a respiratory infection, dermal infection, and a viral infection that causes cancer in a subject.

* * * * *